US007756560B2

(12) United States Patent
Frey et al.

(10) Patent No.: US 7,756,560 B2
(45) Date of Patent: Jul. 13, 2010

(54) SENSOR ARRANGEMENT AND METHOD FOR OPERATING A SENSOR ARRANGEMENT

(75) Inventors: Alexander Frey, Taufkirchen (DE);
Christian Paulus, Weilheim (DE);
Meinrad Schienle, Ottobrunn (DE);
Roland Thewes, Grobenzell (DE)

(73) Assignee: Siemens Aktiengesellschaft, Munich (DE)

( * ) Notice: Subject to any disclaimer, the term of this patent is extended or adjusted under 35 U.S.C. 154(b) by 1615 days.

(21) Appl. No.: 11/002,736

(22) Filed: Dec. 2, 2004

(65) Prior Publication Data
US 2005/0194250 A1 Sep. 8, 2005

Related U.S. Application Data

(63) Continuation of application No. PCT/DE03/01751, filed on May 30, 2003.

(30) Foreign Application Priority Data
Jun. 3, 2002 (DE) ................. 102 24 567

(51) Int. Cl.
*A61B 5/05* (2006.01)
(52) U.S. Cl. .................. 600/345; 204/403.01
(58) Field of Classification Search ........ None
See application file for complete search history.

(56) References Cited

U.S. PATENT DOCUMENTS 5,126,022 A * 6/1992 Soane et al. ............. 204/458
5,264,104 A * 11/1993 Gregg et al. ............ 204/403.09
5,756,355 A * 5/1998 Lang et al. ................ 435/7.21

(Continued)

FOREIGN PATENT DOCUMENTS

DE 196 10 115 A1 9/1997

(Continued)

OTHER PUBLICATIONS

Manfred Paeschke, et al., "Voltammetric Multichannel Measurements Using Silicon Fabricated Microelectrode Arrays", Electroanalysis, Jul. 27, 1996, vol. 7, No. 1, pp. 1-8.

(Continued)

*Primary Examiner*—Patricia C Mallari
*Assistant Examiner*—Karen E Toth
(74) *Attorney, Agent, or Firm*—Dickstein, Shapiro, LLP.

(57) ABSTRACT

Sensor arrangement having capture molecules immobilized on any of three sensor electrodes, wherein molecules to be detected can hybridize with the capture molecules; a control circuit for applying a first electrical signal to a selected sensor electrode and simultaneously applying a second electrical signal to at least two of the other sensor electrodes; a detection device, wherein in a first operating state a reference liquid is introduced into the sensor arrangement and a reference value of an electrical signal is detected at the selected sensor electrode, and in a second operating state an analyte possibly having molecules to be detected is introduced into the sensor arrangement and a sensor value of the electrical signal is detected at the selected sensor electrode; and an evaluation circuit, which, on the basis of the reference value and the sensor value, determines whether a hybridization event has taken place at the selected sensor electrode.

26 Claims, 15 Drawing Sheets

U.S. PATENT DOCUMENTS

| | | | | |
|---|---|---|---|---|
| 6,176,990 | B1 * | 1/2001 | Yager et al. | 204/601 |
| 6,770,190 | B1 * | 8/2004 | Milanovski et al. | 205/777.5 |
| 6,787,368 | B1 * | 9/2004 | Wong et al. | 436/518 |
| 6,942,771 | B1 * | 9/2005 | Kayyem | 204/409 |
| 7,087,148 | B1 * | 8/2006 | Blackburn et al. | 205/452 |
| 7,123,029 | B2 * | 10/2006 | Frey et al. | 324/686 |
| 7,208,077 | B1 * | 4/2007 | Albers et al. | 205/782 |
| 7,351,376 | B1 * | 4/2008 | Quake et al. | 422/100 |
| 7,419,784 | B2 * | 9/2008 | Dubrow et al. | 435/6 |
| 2002/0028503 | A1 * | 3/2002 | Ackley et al. | 435/287.2 |
| 2004/0219547 | A1 * | 11/2004 | Frey et al. | 435/6 |
| 2006/0228657 | A1 * | 10/2006 | Masters et al. | 430/954 |

FOREIGN PATENT DOCUMENTS

| | | |
|---|---|---|
| DE | 201 11 754 U1 | 11/2001 |
| WO | WO-93-22678 A2 | 11/1993 |
| WO | WO-96/33403 A1 | 10/1996 |
| WO | WO-97/21094 A1 | 6/1997 |
| WO | WO 98/37409 * | 8/1998 |
| WO | WO-98/57157 A1 | 12/1998 |
| WO | WO-01/42508 A2 | 6/2001 |
| WO | WO-01/75151 A2 | 10/2001 |

OTHER PUBLICATIONS

R. Hintsche, et al., "Microbiosensors using electrodes made in Si-technology", Frontiers in Biosensorics I—Fundamental Aspects, F.W. Scheller et al. ed., 1997, Birkhauser Verlag Basle.

Peter Van Gerwen, et al., "Nanoscaled Interdigitated Electrode Arrays for Biochemical Sensors", Transducers '97, Jun. 16-19, 1997, 1997 International Conference on Solid-State Sensors and Actuators, pp. 907-910.

Christian Krause, et al., "Capacitive Detection of Surfactant Adsorption on Hydrophobized Gold Electrodes", Langmuir, 1996, vol. 12, No. 25, pp. 6059-6064.

Vladimir M. Mirsky, et al., "Capacitive monitoring of protein immobilization and antigen-antibody reactions on monomolecular alkylthiol films on gold electrodes", Biosensors & Bioelectronics, 1997, vol. 12, No. 9-10, pp. 977-989.

Michael Riepl, et al., "Electrical Control of Alkanethiols Self-Assembly on a Gold Surface as an Approach for Preparation of Microelectrode Arrays", Mikrochim. Acta 131, 1999, pp. 29-34.

* cited by examiner

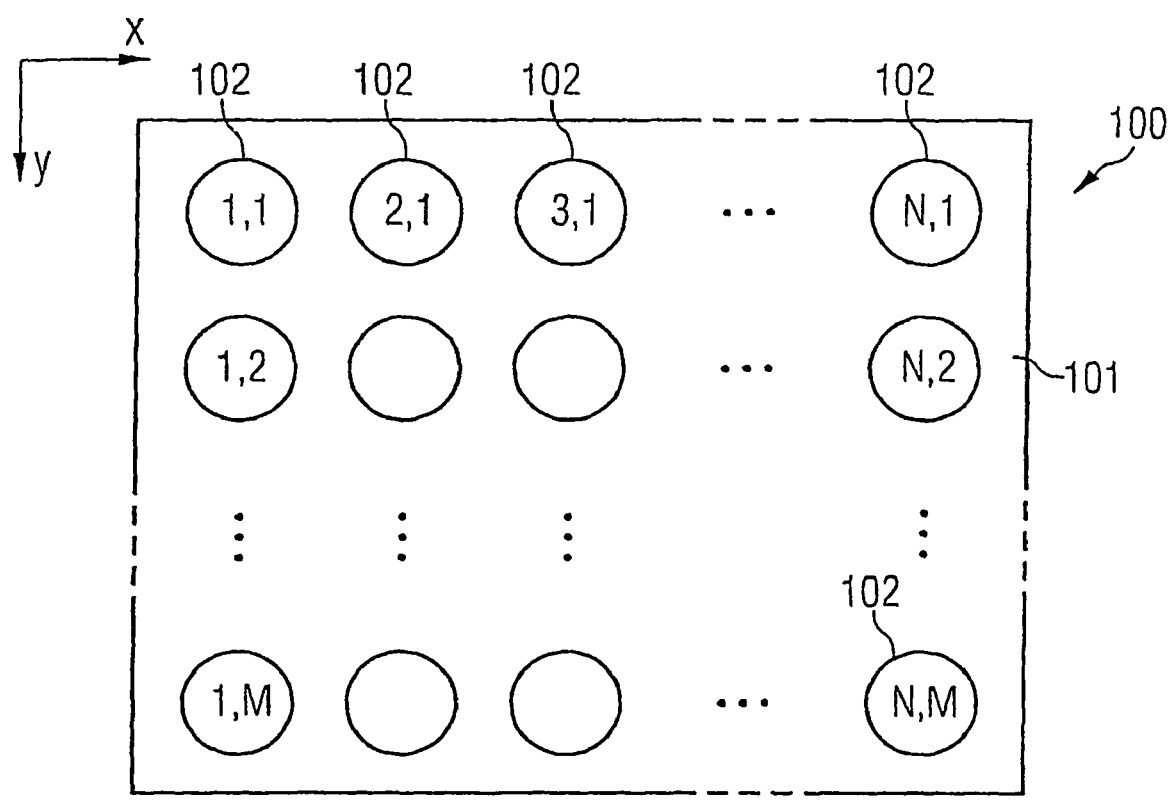
FIG 1  Stand der Technik

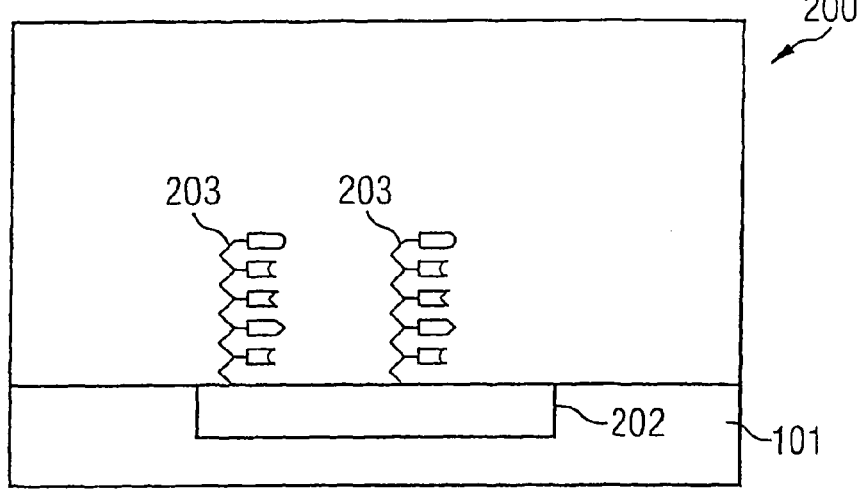
FIG 2A Stand der Technik
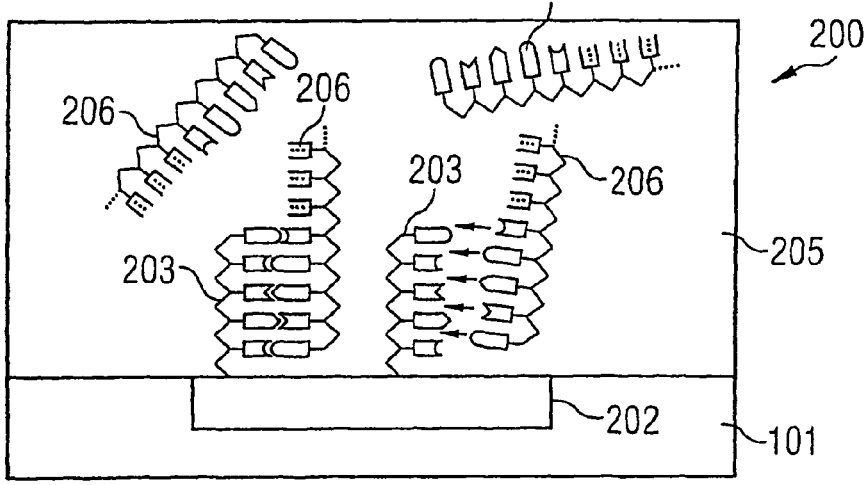
FIG 2B Stand der Technik
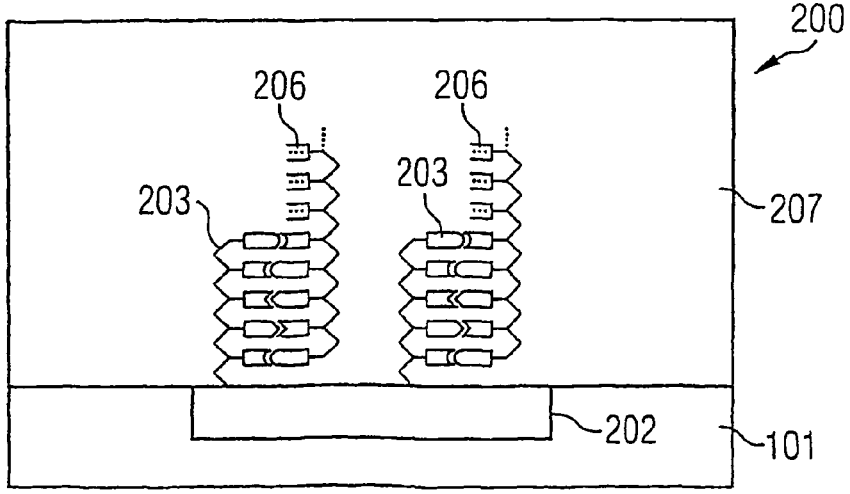
FIG 2C Stand der Technik

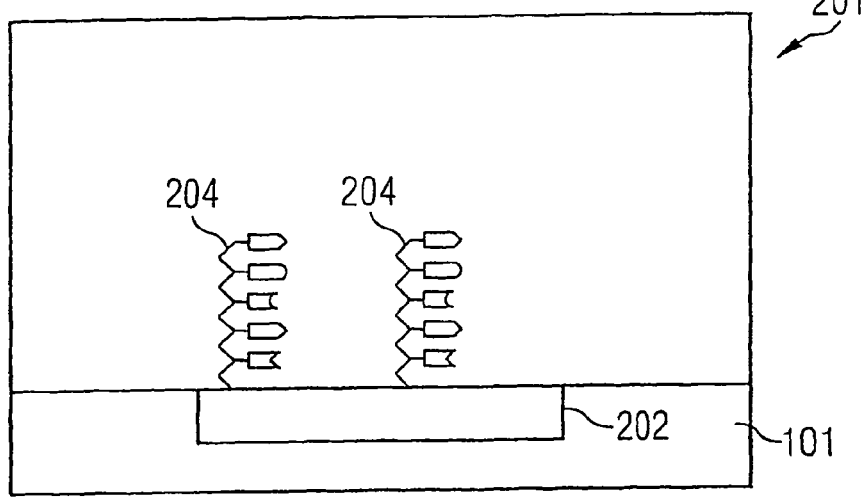
FIG 2D Stand der Technik
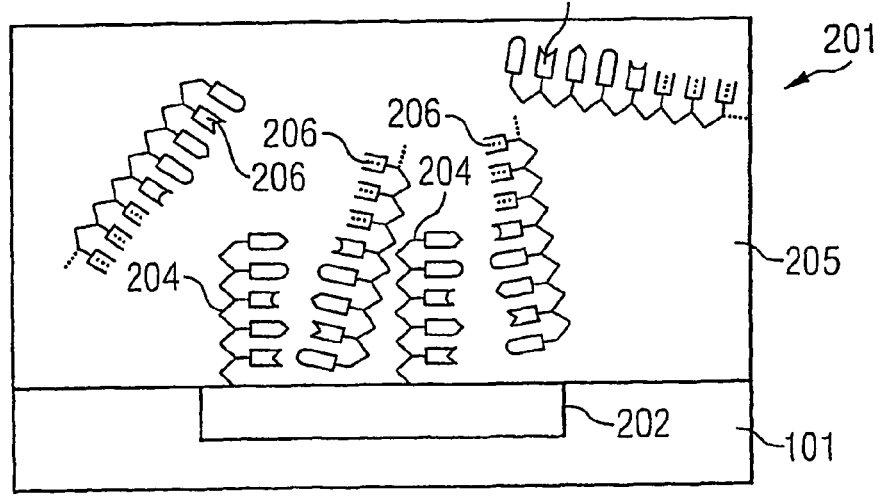
FIG 2E Stand der Technik
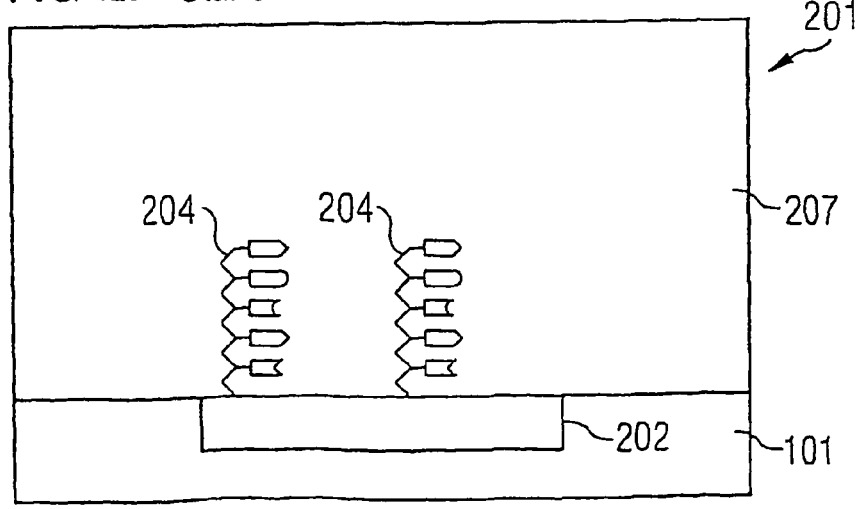
FIG 2F Stand der Technik

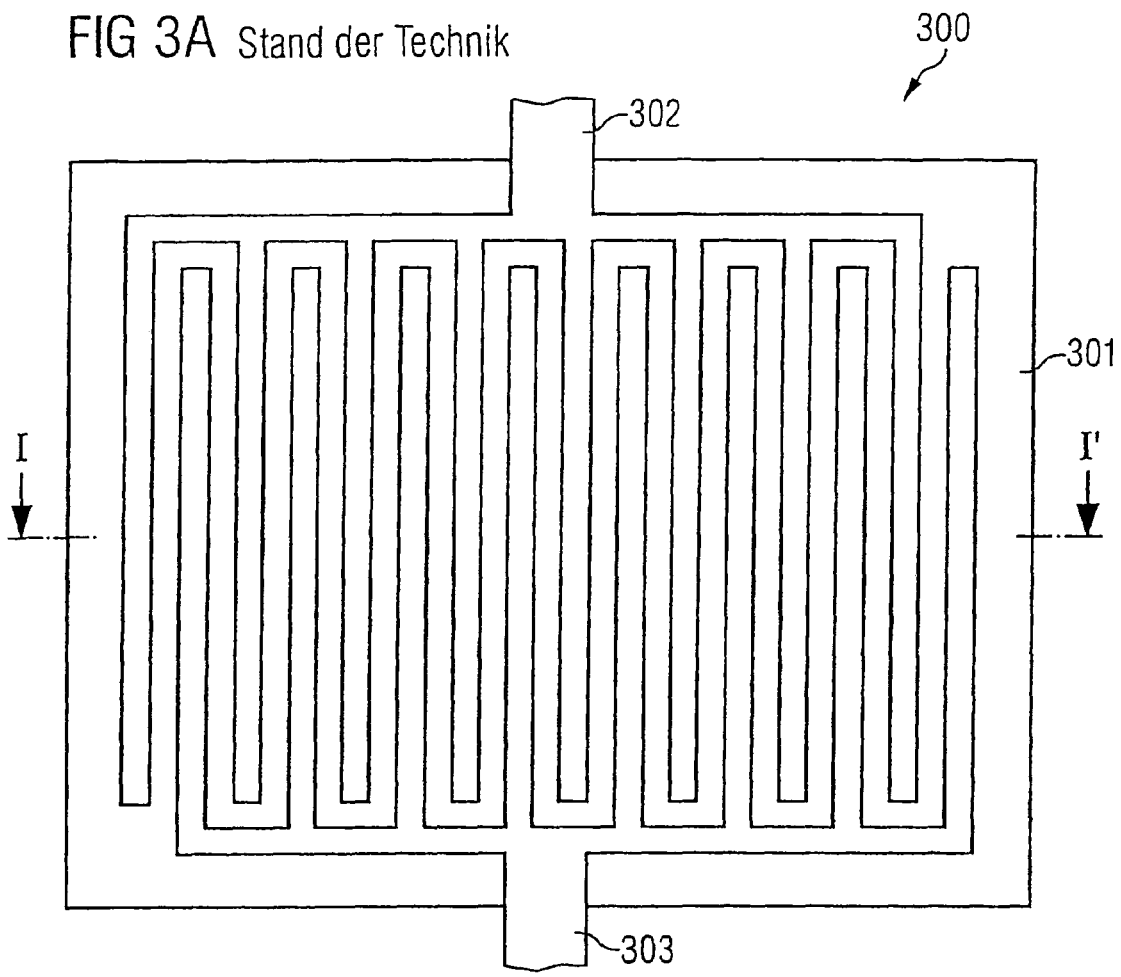
FIG 3A Stand der Technik
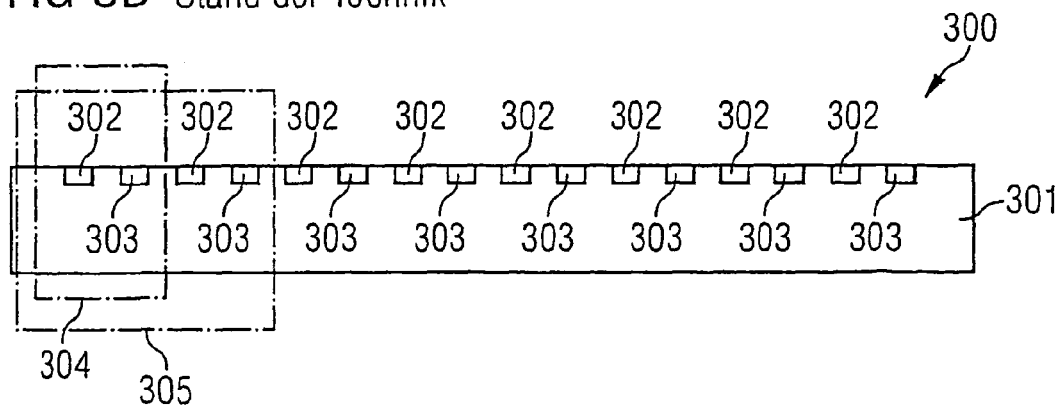
FIG 3B Stand der Technik

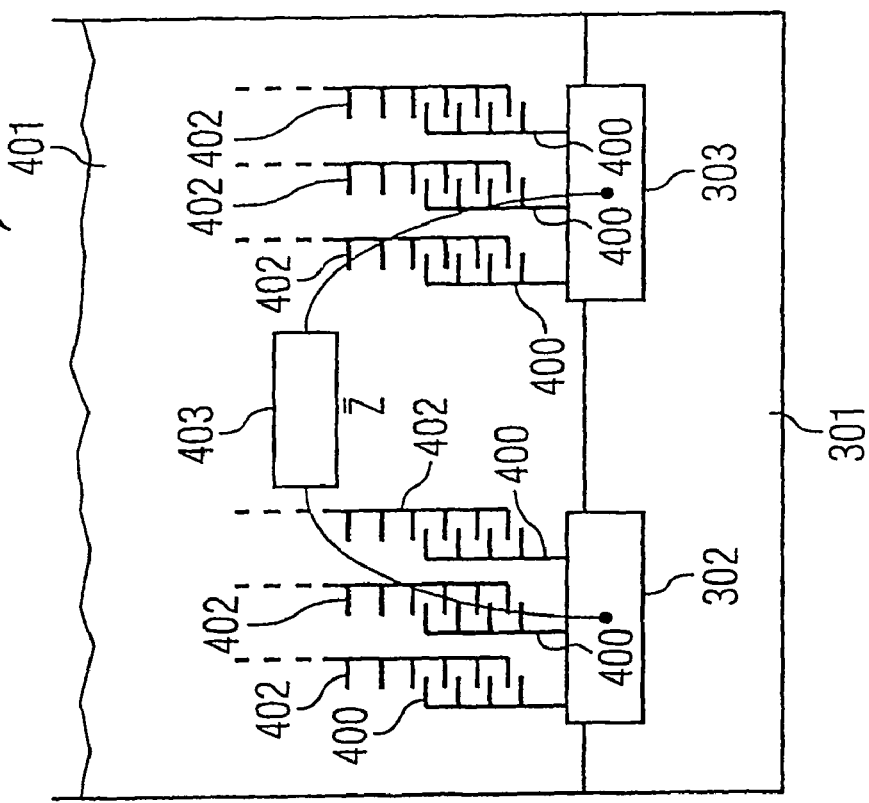
FIG 4B  Stand der Technik
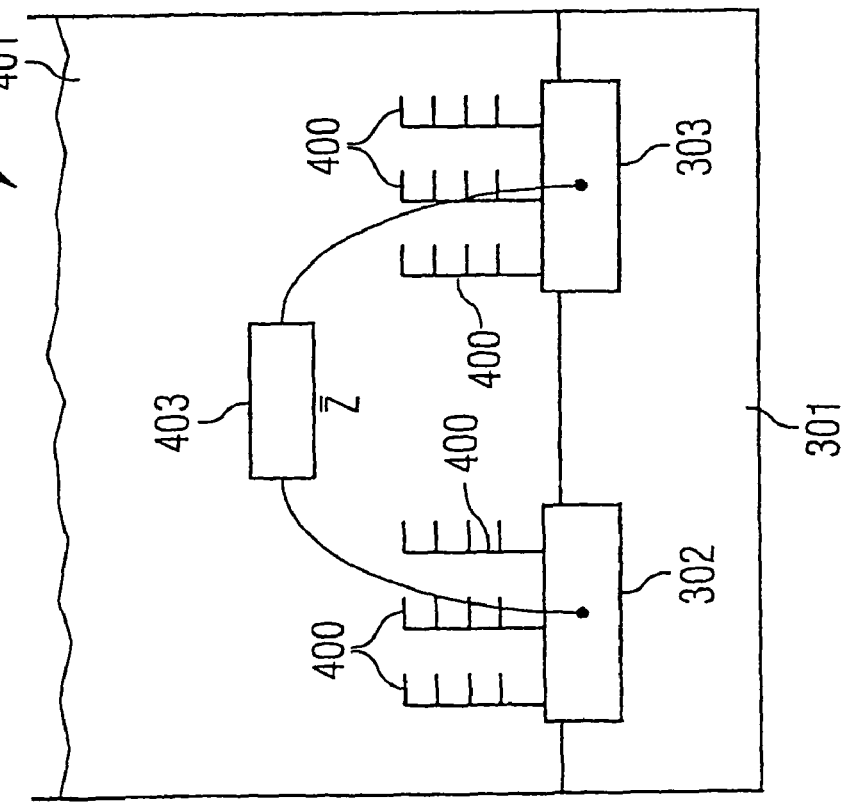
FIG 4A  Stand der Technik

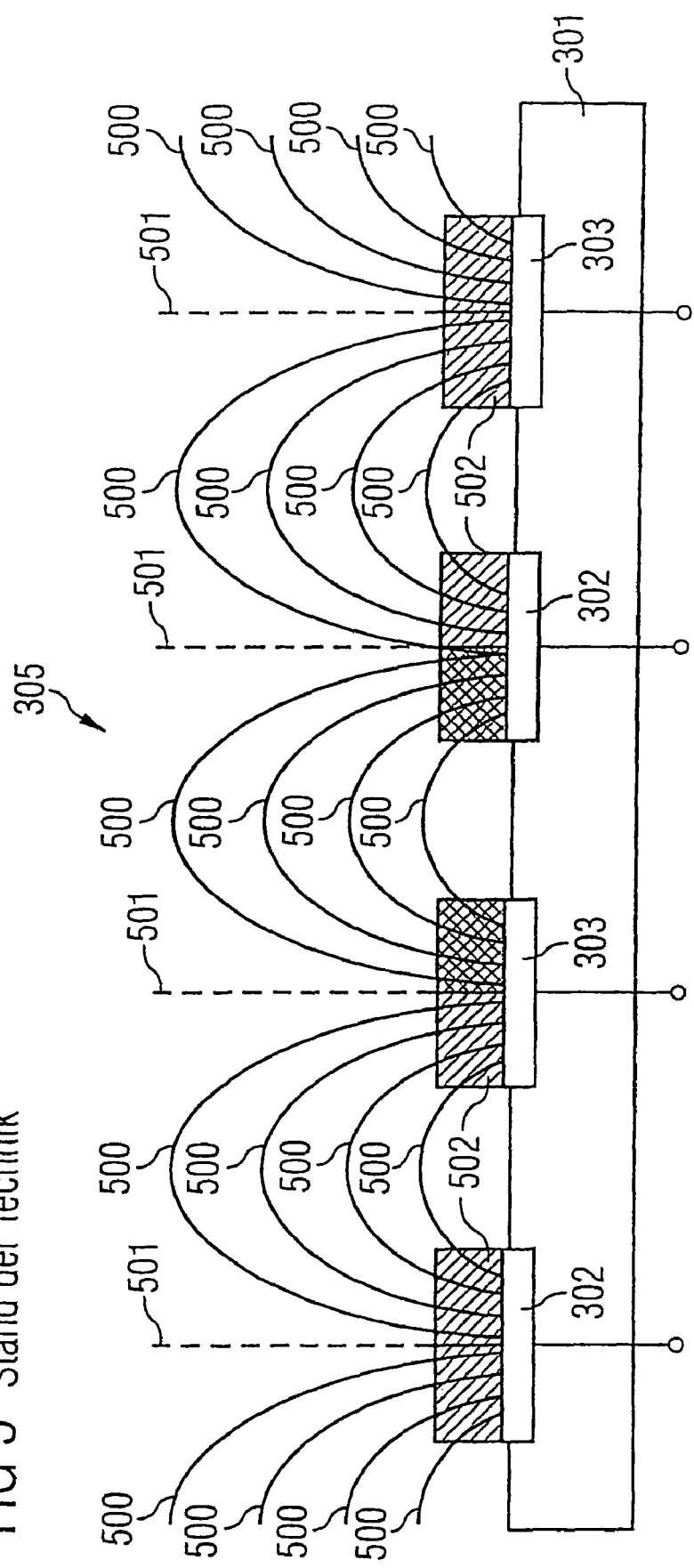
FIG 5 Stand der Technik

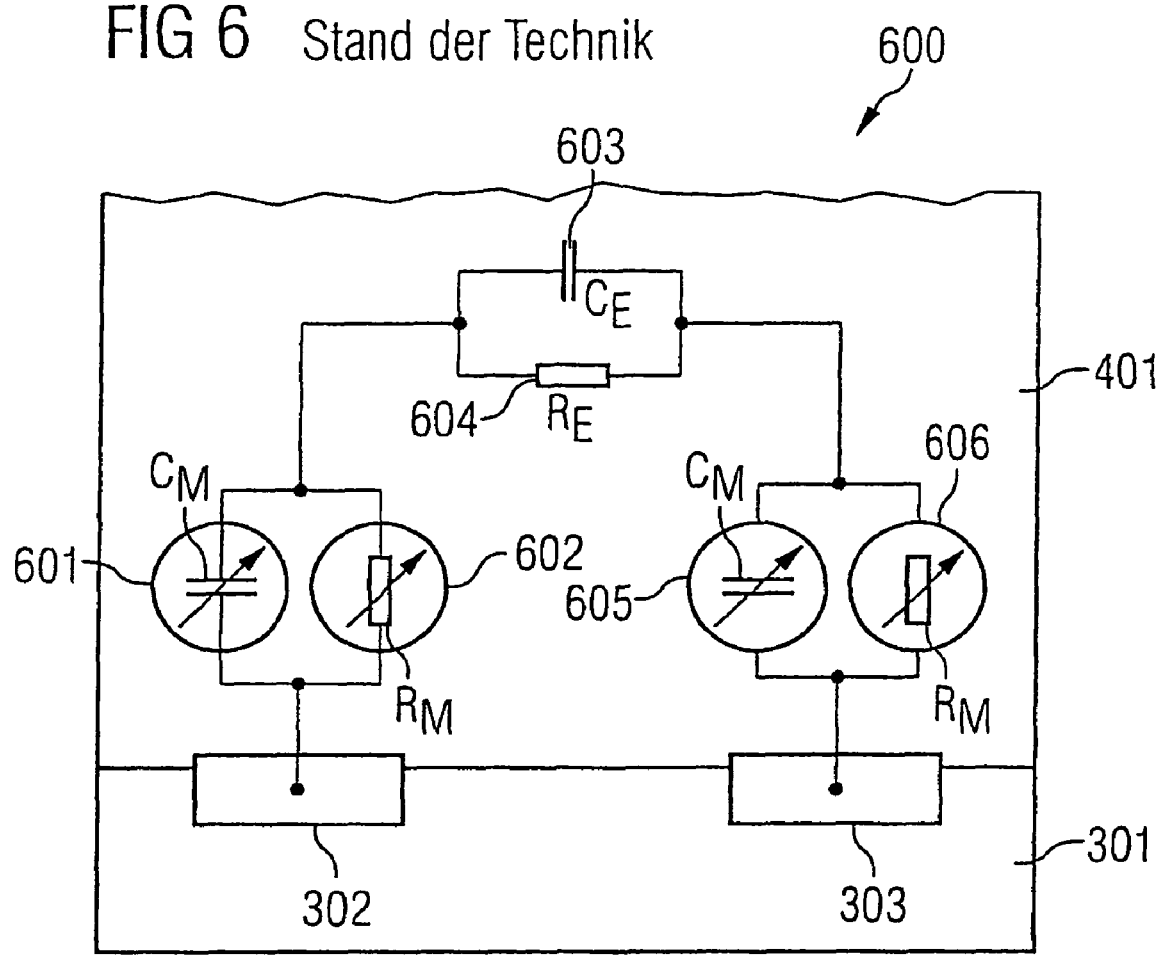
FIG 6  Stand der Technik

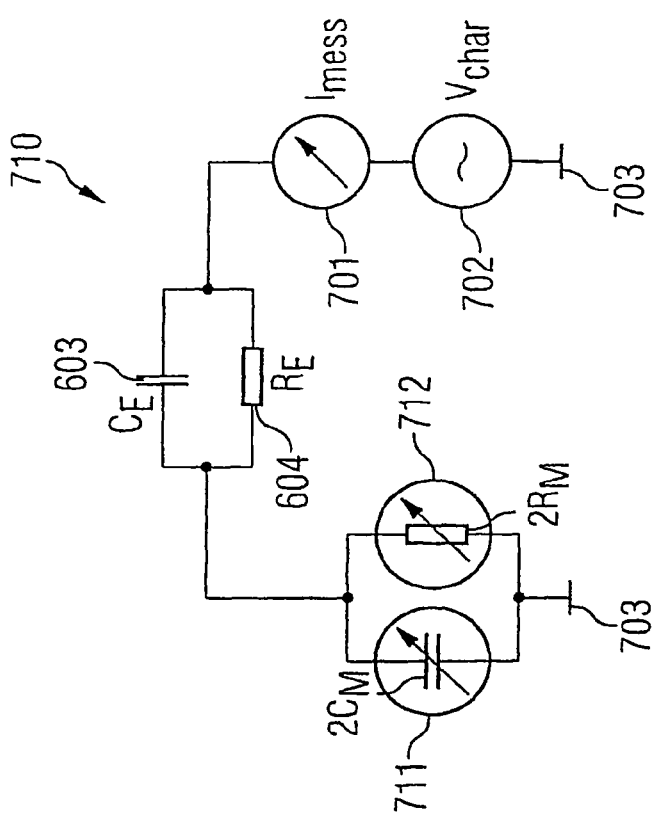
FIG 7A Stand der Technik
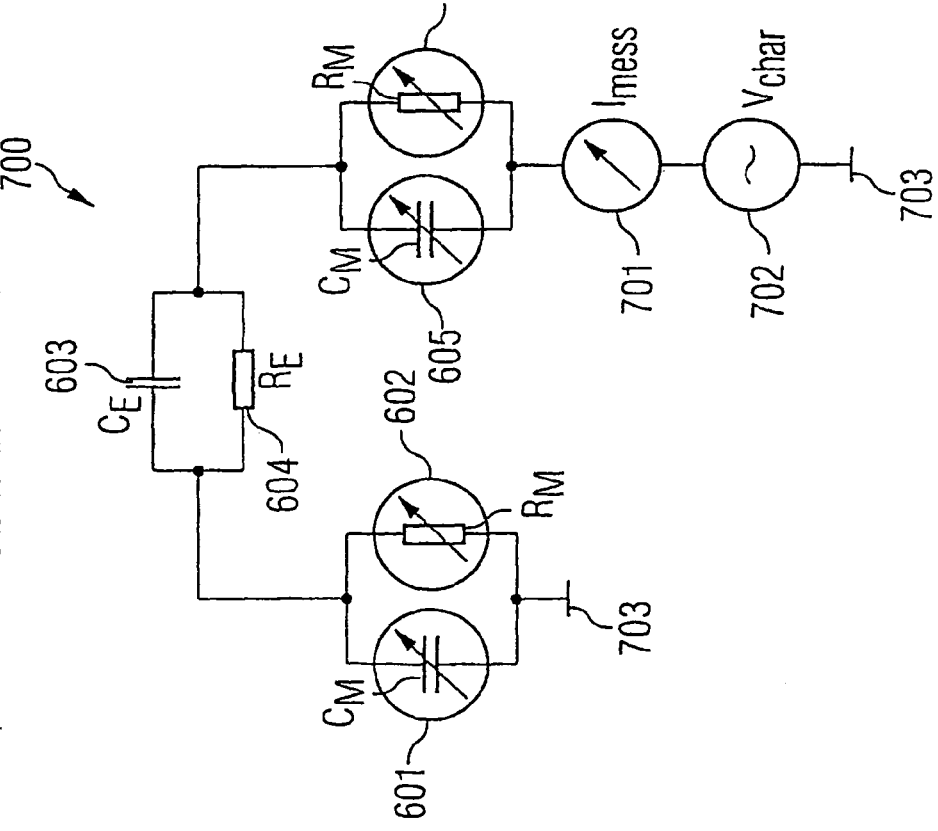
FIG 7B Stand der Technik

FIG 8A Stand der Technik
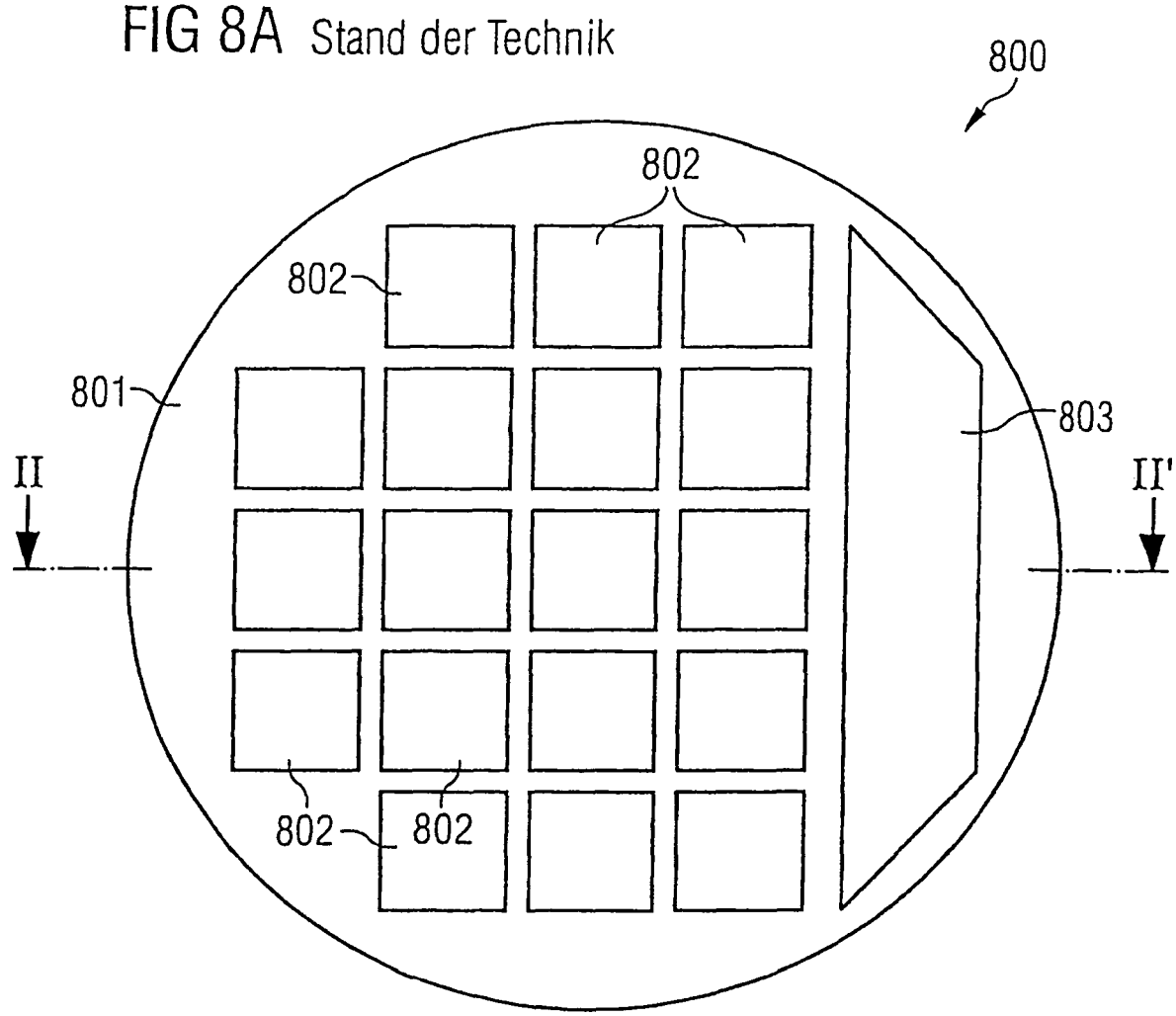
FIG 8B Stand der Technik
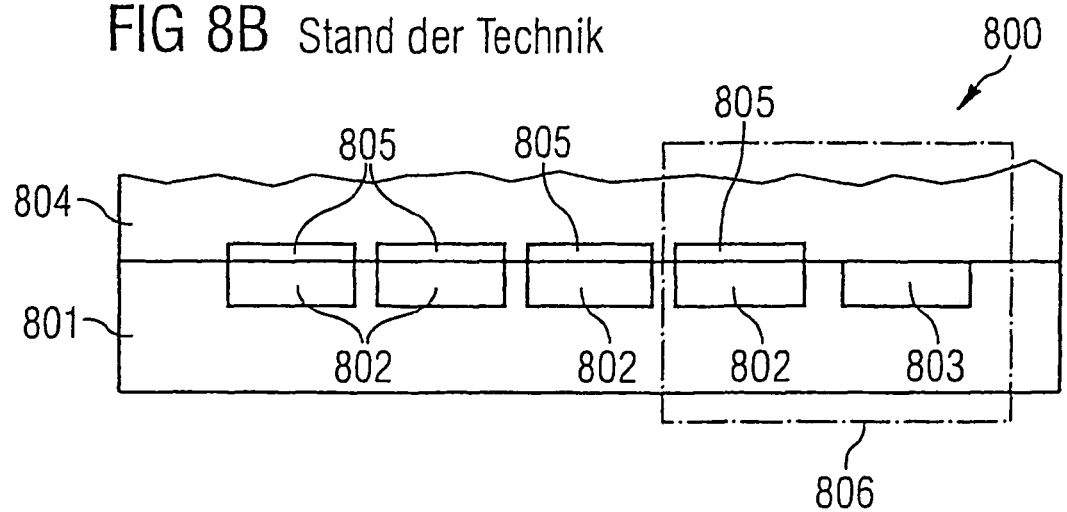

FIG 9  Stand der Technik
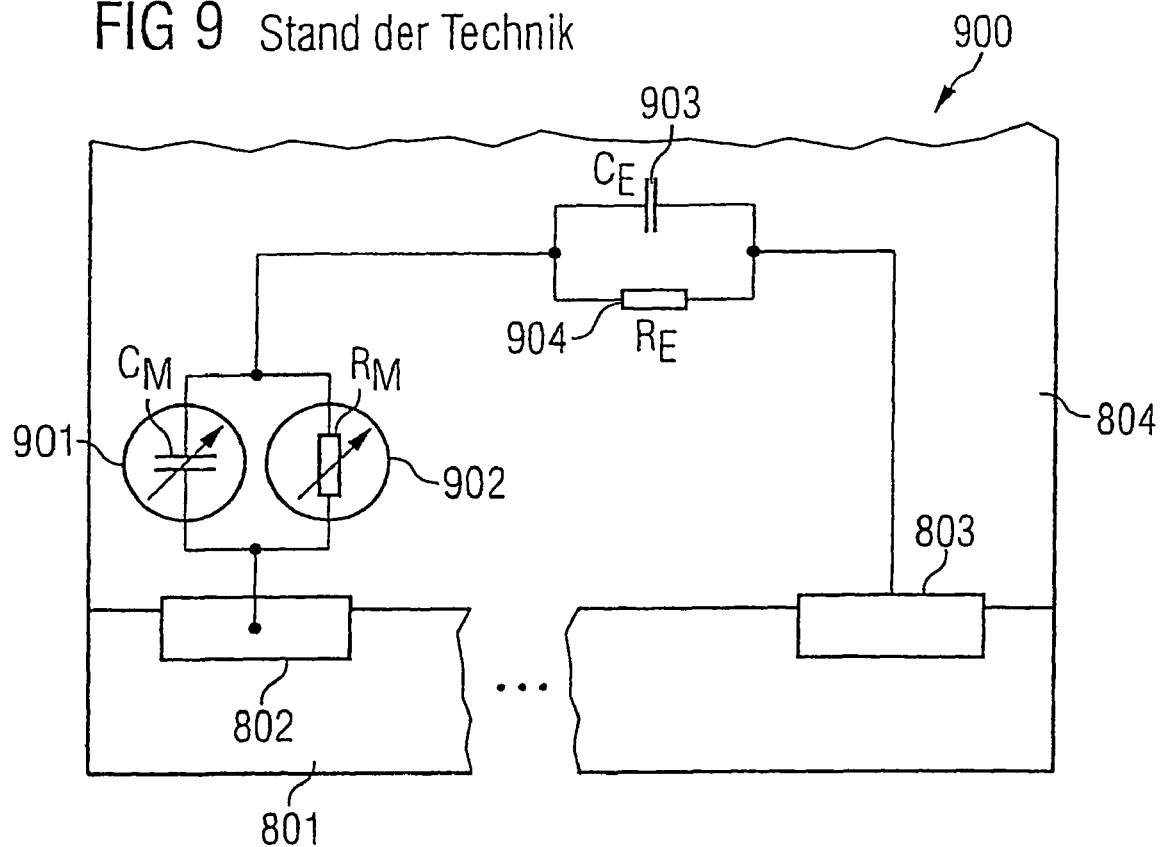
FIG 10  Stand der Technik
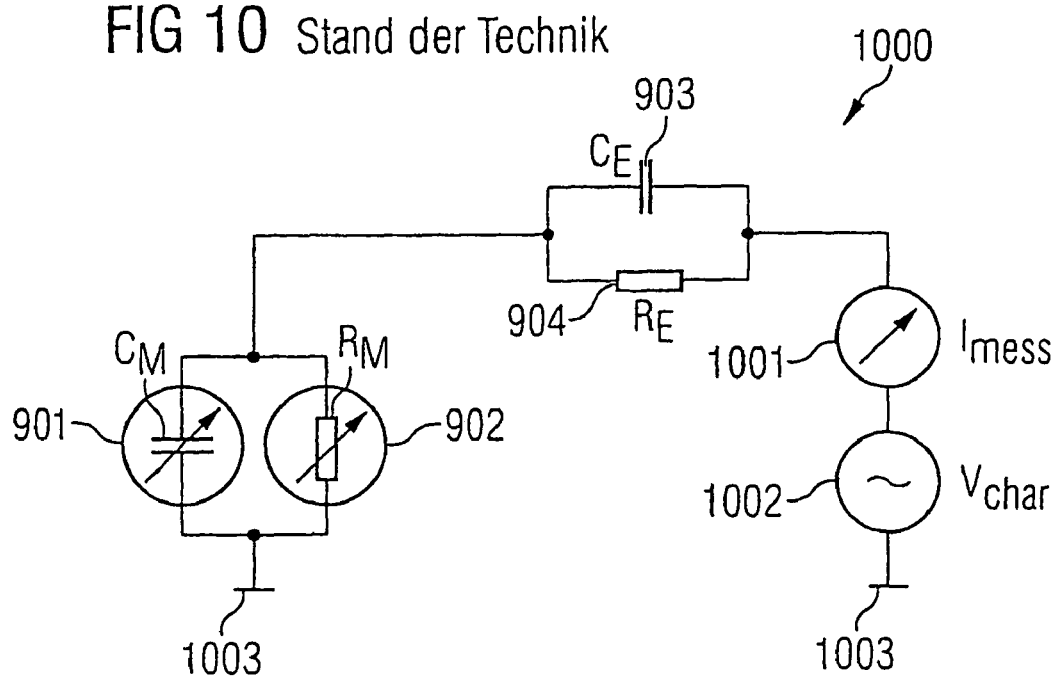

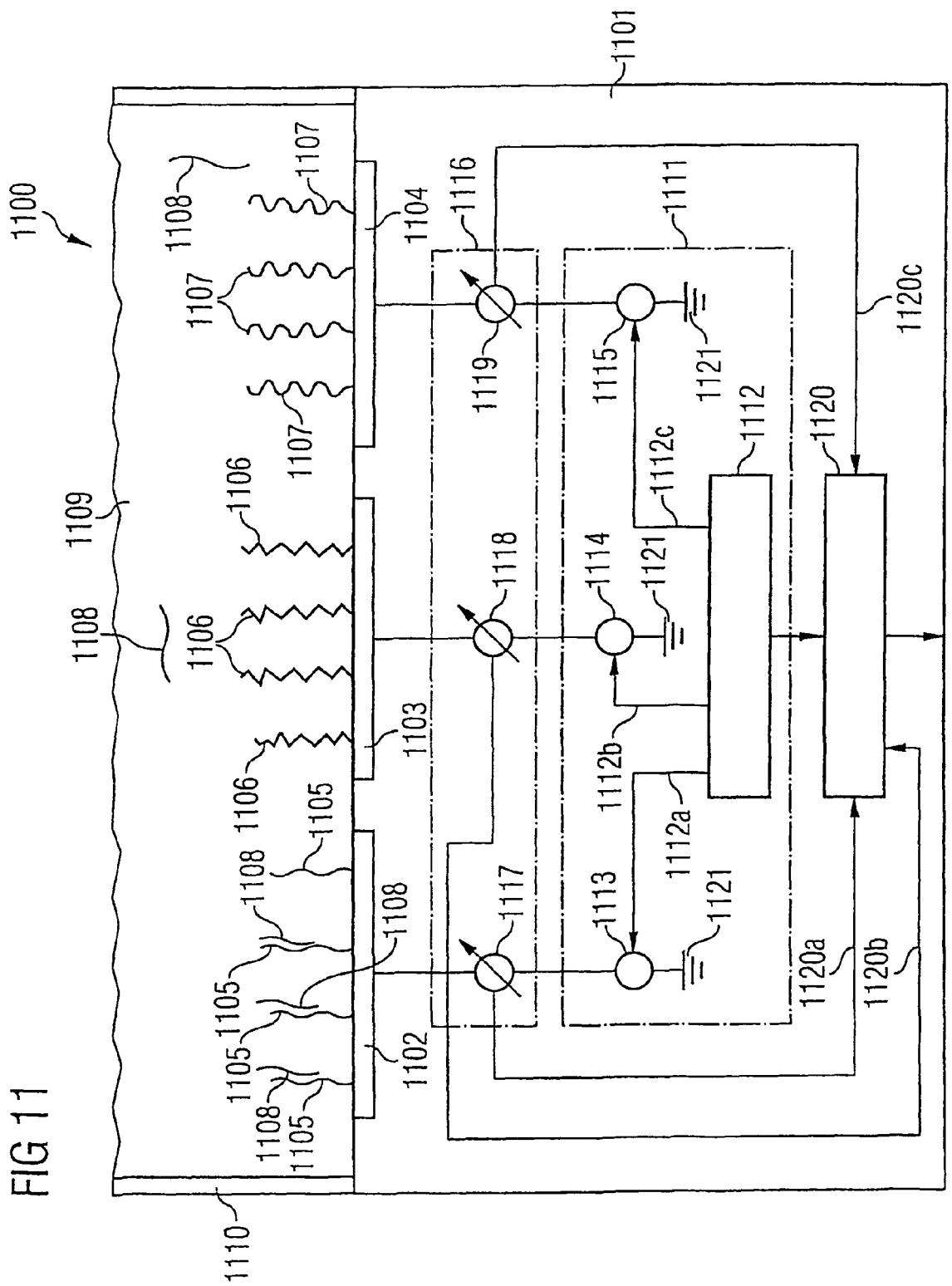

SENSOR ARRANGEMENT AND METHOD FOR OPERATING A SENSOR ARRANGEMENT

CROSS-REFERENCE TO RELATED APPLICATION

This application is a continuation of International Patent Application Serial No. PCT/DE03/01751, filed May 30, 2003, which published in German on Dec. 11, 2003 as WO 03/102602.

FIELD OF THE INVENTION

The invention relates to a sensor arrangement and a method for operating a sensor arrangement.

BACKGROUND OF THE INVENTION

Biosensor arrays and chemosensor arrays serve for detecting molecules in an analyte to be examined. Such arrays are increasingly being realized on chips for the purpose of miniaturization. The sensors are often arranged in a large number on a substrate. The substrate may be a semiconductor chip (silicon) for example, particularly for the case where functions of an integrated electronic circuit are intended to be realized. Such substrates may alternatively be produced from glass, plastic or another material provided that no or only comparatively simple electronics are required for operating them. The high degree of parallelization enables a simultaneous parallel implementation of different tests, for example tests for the presence of different substances (e.g. molecules) in a predetermined analyte. On account of this property, such sensor arrangements including a corresponding evaluation system obtain diverse applications in medical diagnosis technology, in the pharmacological industry (e.g. for pharmacological screening, "high throughput screening", HTS), in the chemical industry, in foodstuffs analysis, and in ecological and foodstuffs technology.

The basic principle of many known sensors is based on the fact that firstly so-called capture molecules are applied, e.g. using microdispensing techniques, and immobilized in a position-specific manner on a chip.

FIG. 1 shows a sensor arrangement 100 known from the prior art, in which a multiplicity of sensor arrays 102 are arranged in matrix form on a chip 101. The sensor arrays 102 are arranged in N columns and in M rows, that is to say at N×M positions, different capture molecules being immobilized on each sensor array.

FIG. 2A to FIG. 2F in each case show a diagrammatic cross-sectional view of one of the sensor arrays 102 shown in FIG. 1. In particular, FIG. 2A to FIG. 2C show a first sensor array 200, and FIG. 2D to FIG. 2F show a second sensor array 201, the different illustrations of the first sensor array 200 in FIG. 2A to FIG. 2C corresponding to three different operating states, and the illustrations in FIG. 2D to FIG. 2F analogously corresponding to three different operating states of the second sensor array 201.

Each of the sensor arrays 200, 201 has a sensor electrode 202 integrated in the chip 101. First capture molecules 203 are immobilized on the sensor electrode 202 of the first sensor array 200, the first capture molecules 203 being DNA half strands. Second capture molecules 204, which differ from the first capture molecules 203, are immobilized on the sensor electrode 202 of the second sensor array 201.

FIG. 2A, FIG. 2D show the first sensor array 200 and the second sensor array 201, respectively, in an operating state in which the sensor arrangement 100 is free of potential binding partners (e.g. DNA half strands).

For the purpose of diagnosis, that is to say for examining an analyte for the presence of specific DNA molecules, an analyte 205 is firstly applied to all the sensor arrays 102 of the sensor arrangement 100 and therefore also to the sensor arrays 200, 201, i.e. the entire sensor arrangement 100 is flooded with the analyte 205 to be examined. This operating state of the first sensor array 200 is shown in FIG. 2B, and of the second sensor array 201 in FIG. 2E. Since the first capture molecules 203 fit together with (half-stranded) DNA molecules present in the analyte 205, namely with the particles 206 to be detected, in accordance with the key/lock principle, a hybridization is effected, i.e. a binding of the respective DNA molecules 206 to the complementary first capture molecules 203 of the first sensor array 200 (cf. FIG. 2B). Since the second capture molecules 204 do not fit together with the particles 206 to be detected on account of their base sequence (cf. FIG. 2E), no hybridization is effected.

In order to obtain the operating states of the first sensor array 200 and of the second sensor array 201 respectively shown in FIG. 2C, FIG. 2F, the analyte 205 is removed from the sensor arrangement 100. Furthermore, a rinsing solution 207 is applied to the sensor arrangement 100. As a result, the particles 206 to be detected that have hybridized with the first capture molecules 206 remain on the first sensor array 200, whereas only the second capture molecules 204, but not particles 206 to be detected, remain on the second sensor array 201.

Optical methods are often used for detecting the hybridization that has taken place.

In an optical method, a fluorescent marker ("label") is bound to the DNA strands present in the analytes. If the entire sensor arrangement 100 is then irradiated with electromagnetic radiation (e.g. light) after a hybridization process that has taken place and after a further rinsing step, this is possible, on the basis of knowledge of the localization of the respective capture molecules 203, 204, to determine the sensor arrays at which a hybridization has taken place (first sensor array 200) and the sensor arrays at which hybridization has not taken place (second sensor array 201). On the basis of the precise knowledge of the capture molecules 203, 204 used, it is possible to deduce the presence or absence of specific particles to be detected in the analyte to be examined with a high selectivity. The optical methods have the disadvantage of needing a complicated and cost-intensive optical system for evaluation. This makes it more difficult for example to use such optical systems in physicians' practices.

As an alternative to the optical method, a hybridization event that has taken place can be detected using an electric method.

In this respect, it is necessary to distinguish between methods based on the use of an enzyme label (described for example in [M. Paeschke et al., Electroanalysis 1996, 7, No. 1, p. 1-8, R. Hintzsche et al., "Microbiosensors using electrodes made in Si-technology", in "Frontiers in Biosensorics I—Fundamental Aspects", F. W. Scheller et al. ed., 1997, Birkhauser Verlag Basle) and so-called "label-free" methods, described for example in WO 9322678, DE 19610115 A1, U.S. Pat. Ser. No. 60/007,840, Peter Van Gerwen et al., Transducers '97, p. 907-910, Christian Krause et al., Langmuir, Vol. 12, No. 25, 1996 p. 6059-6064, V. M. Mirsky, Biosensors & Bioelectronics 1997, Vol. 12 No. 9-10, pp. 977-989, and M. Riepl et al, Mikrochim. Acta, 29-34, 1999. Label-free methods are more attractive since a method step for providing molecules with a label, which method step is often complicated from a biochemical standpoint, is avoided and a label-free method is therefore simpler, more robust in respect of errors and less expensive.

However, the operation of an electronic biosensor is difficult to realize, so that, particularly in the case of the electronic label-free methods, hitherto examinations have been implemented only on individual sensors or on very small arrays comprising a stringing together of individual sensors.

Label-free methods known from the prior art are described below.

A first approach is disclosed in WO 9322678, DE 19610115 A1, U.S. Patent Ser. No. 60/007,840, and Peter Van Gerwen et al. This approach is described below with reference to FIG. 3A to FIG. 7B.

FIG. 3A, FIG. 3B show an interdigital electrode arrangement 300 in which a first electrode structure 302 and a second electrode structure 303 are applied in a substrate 301, said electrode structures clearly meshing in interdigitated fashion. FIG. 3A shows a plan view of the interdigital electrode arrangement 300 and FIG. 3B shows a cross-sectional view along the section line I-I' shown in FIG. 3A. The interdigital electrode arrangement 300 contains periodic electrode components—arranged one beside the other—of the electrode structures 302, 303.

In order to explain the principle of the functioning of the interdigital electrode arrangement 300, a first partial region 304 of the interdigital electrode arrangement 300 will be described with reference to FIG. 4A, FIG. 4B.

The first partial region 304 is shown in a first operating state as a cross-sectional view in FIG. 4A and in a second operating state as a cross-sectional view in FIG. 4B.

Capture molecules 400 are in each case immobilized on the electrode structures 302, 302. Gold material is preferably used for the electrode structures 302, 302, so that the immobilization of the capture molecules 400 is realized using the particularly advantageous gold-sulfur coupling known from biochemistry, for example by a thiol terminal group (SH group) of the capture molecules 400 being chemically coupled to the gold electrodes 302, 303.

An electrolytic analyte 401 to be examined, which is again intended to be examined for the presence of particles 402 to be detected (for example specific DNA molecules), is situated above the sensor electrodes 302, 303 during active sensor operation. A hybridization, that is to say a binding of DNA strands 402 to the capture molecules 400, is effected only when the capture molecules 400 and the DNA strands 402 match one another in accordance with the key/lock principle (cf. FIG. 4B). If this is not the case, then no hybridization is effected. The specificity of the sensor is thus derived from the specificity of the capture molecules 400.

The electrical parameter that is evaluated in the case of this measurement is the impedance 403 between the electrodes 302, 303, which is illustrated diagrammatically in FIG. 4A, FIG. 4B. On account of a hybridization that has taken place, the value of the impedance changes since the DNA particles 402 to be detected and the capture molecules 400 comprise a material having electrical properties that deviate from the material of the electrolyte and, after the hybridization, the electrolyte is clearly displaced from the volume surrounding the electrodes 302, 303.

FIG. 5 shows a second partial region 305 of the interdigital electrode arrangement 300 in a cross-sectional view. The second partial region 305 represents a larger partial region of the interdigital electrode arrangement 300 than the first partial region 304 illustrated in FIG. 4A, FIG. 4B. FIG. 5 diagrammatically shows the profile of the electric field lines 500 between respectively adjacent electrode structures 302, 303. As is furthermore shown in FIG. 5 the field profiles are periodic within a respective imaginary region through two lines of symmetry 501, so that the consideration of two directly adjacent electrode structures 302, 303 that is shown in FIG. 4A, FIG. 4B is sufficient. Furthermore, FIG. 5 diagrammatically shows a coverage region 502 for each of the electrode structures 302, 303, said coverage region representing the capture molecules immobilized on the electrode structures 301, 302 and particles to be detected that have possibly hybridized with said capture molecules. It can clearly be understood from the illustration shown in FIG. 5 that the profile of the field lines 500 is significantly influenced on account of a hybridization event since the physicochemical properties particularly of the coverage region 502 are altered.

It should furthermore be noted that, supplementarily or alternatively, capture molecules may be provided in regions between electrodes 302, 303. The electrical properties of the electrodes again change in the case of hybridization events between capture molecules provided in regions between the electrodes and particles to be detected.

FIG. 6 diagrammatically shows a simplified equivalent circuit diagram 600 of the first partial region 304 of the interdigital electrode arrangement 300 shown in FIG. 4A.

The equivalent circuit diagram 600 shows a variable first capacitance 601 $C_M$, the value of which is dependent on the extent of a hybridization effected at the electrode structure 302. A variable first nonreactive resistance 602 $R_M$ is connected in parallel with said capacitance. Clearly, the components 601, 602 represent the electrical properties of the surrounding region of the first electrode structure 302. The diagram furthermore shows a variable second capacitance 603 $C_E$ and a variable second nonreactive resistance 604 $R_E$ connected in parallel therewith, which represents the electrical properties of the analyte 401. Moreover, the diagram shows a variable third capacitance 605 $C_M$ and a variable third nonreactive resistance 606 $R_M$ connected in parallel therewith, representing the electrical properties of the surrounding region of the second electrode structure 303. As is furthermore shown in FIG. 6, the parallel circuit comprising components 601, 602, the parallel circuit comprising components 603, 604 and the parallel circuit comprising components 605, 606 are connected in series. The components 601 to 606 are represented in variable fashion in order to illustrate that their values change on account of a sensor event.

In order to determine the value of the impedance, an AC voltage $V_{char}$ is applied to one of the electrodes 302, 303, as shown in the equivalent circuit diagram 700 of the first partial region 304 shown in FIG. 7A. The AC voltage $V_{char}$ is provided using an AC voltage source 702. The current $I_{meas}$ flowing through the arrangement is detected using the ammeter 701. The components 701, 702 are connected in series with one another and are connected between the parallel circuit comprising components 605, 606 and the electrical ground potential 703. The AC current signal $I_{meas}$ resulting at the electrodes 302, 303 is evaluated together with the applied AC voltage $V_{char}$ in order to determine the impedance. As an alternative, a signal, that is to say an electrical voltage, may also be applied in each case to both electrodes 302, 303, the signals then being in antiphase.

The version of a simplified equivalent circuit diagram 710 shown in FIG. 7B differs from the equivalent circuit diagram 700 shown in FIG. 7A in that the elements $C_M$ 601, 605 and $R_M$ 602, 606 have been combined to form a first effective capacitance 711 and, respectively, to form a first effective nonreactive resistance 712.

The distance between the electrodes 302, 303 is typically in the sub-μm range. In accordance with the interdigital electrode arrangement 300, a multiplicity of electrode components (clearly fingers) of the electrode structures 302 and 303 are arranged parallel. Circular arrangements are used in WO 9322678, DE 19610115 A1, U.S. Patent Ser. No. 60/007,840, and Peter Van Gerwen et al. for reasons of fluidics. The external dimensions or the diameter of such individual sensors is in the range of from several hundred Am to the single-digit mm range.

With regard to the exciting AC voltage $V_{char}$, it should be taken into account that its root-mean-square value or its peak value ought not to exceed a specific maximum value. The biochemical or electrochemical boundary conditions enabling the operation of such sensors are violated when such a maximum value is exceeded. If the electrode potential (which is referred to the electrical potential of the electrolyte) exceeds an upper threshold value, then specific substances may be oxidized in a surrounding region of an electrode. If the electrical potential (which is referred to the electrical potential of the electrolyte) falls below a lower threshold value, substances are reduced there. An undesirable oxidation or reduction may have the effect, inter alia, of breaking up the chemical bond entered into during immobilization and hybridization. Furthermore, electrolysis may commence at the sensor electrodes, so that the electrolysis products bring the chemical milieu required for operation of the sensors out of the required equilibrium or lead to gas formation. The absolute values of the critical potentials depend on the composition and the concentration ratio and the chemical surroundings of the electrodes (for example immobilization layer, analyte, etc.).

Typical values for the exciting voltage lie in the range of a few 10 mV to at most around 100 mV. This is an important boundary condition for the operation of such sensors since the resulting measurement signal (current intensity $I_{meas}$), with regard to its magnitude, is approximately directly proportional to the applied voltage.

A second principle of a label-free electrical sensor such as is disclosed in Christian Krause et al., V. M. Mirsky, and M. Riepl et al. is described below with reference to FIG. 8 to FIG. 10.

In accordance with this second approach, a planar electrode is in each case used for the detection of a species, that is to say for the immobilization of capture molecules and for hybridization with particles to be detected. Furthermore, an AC voltage signal is applied directly to an electrically conductive analyte. In the case of these methods, the application of the AC voltage and the optionally required additional application of a DC offset are effected using a so-called counterelectrode or reference electrode, which realizes a low-impedance electrical coupling to the electrolyte, which electrical coupling is always defined under changing electrochemical conditions and is constant in terms of its electrical properties. Such a reference electrode is usually produced from a different material (for example silver/silver chloride) than the electrodes that are utilized for immobilizing the capture molecules and are therefore often produced from gold material. The use of different materials results from the different electrochemical requirements made of the two electrode materials.

FIG. 8A, FIG. 8B show a sensor arrangement 800 in accordance with this second approach. FIG. 8A shows a plan view of the sensor arrangement 800 and FIG. 8B shows a cross-sectional view along a section line II-II' from FIG. 8A.

As is shown in FIG. 8A, a plurality of sensor arrays 802 and a common reference electrode 803 are arranged on a silicon substrate 801. Provided on the surface of each sensor array 802 is an active region 805, on which capture molecules are immobilized, for hybridization with complementary particles to be detected. An analyte 804 is filled into the sensor arrangement 800. The sensor arrangement 800 uses a silicon substrate 801, although the electrical properties of the silicon are not utilized, in order to form powerful integrated electronics therein.

FIG. 9 shows an equivalent circuit diagram 900 of a partial region 806 of the sensor arrangement 800. This shows a variable first capacitance 901 $C_M$, which represents the capacitance of the surrounding region of the sensor array 802. Furthermore, a variable first nonreactive resistance 902 $R_M$ connected in parallel therewith is shown, representing the nonreactive resistance of the surrounding region of the sensor array 802. A variable second capacitance 903 $C_E$ and a variable second nonreactive resistance $R_E$ 904 connected in parallel therewith represent the electrical properties of the analyte 804.

Furthermore, FIG. 10 shows a further equivalent circuit diagram 1000 of the partial region 806 of the sensor arrangement 800. The latter exhibits, in addition to the components shown in FIG. 9, an AC voltage source 1002, by means of which an AC voltage can be applied, and exhibits an ammeter 1001 for detecting a measurement current $I_{meas}$. The components 1001, 1002 connected in parallel are connected between the electrical ground potential 1003 and the parallel circuit comprising components 903, 904.

Often only very small sample volumes are available in biochemistry. In this case, the use of the sensor arrangement 800 is disadvantageous since the counterelectrode 803 can be provided in miniaturized form only in a very complicated manner, or not at all. It is often realized by a small chlorinated silver tube.

In the case of the described sensor arrangements known from the prior art, the problem occurs during operation or evaluation of measurement signals that the impedance between the electrodes does not have exclusively capacitive components, but rather is a relatively complex, composite quantity. A fundamental reason for this is that, at the measurement electrode, that is in direct electrical (galvanic) contact with the electrolyte, an electrochemical conversion always takes place which is at equilibrium only precisely when the electrical potential of the electrode with respect to the electrolyte can be set freely. Any displacement of this electrical potential automatically results in a net conversion of material at the electrodes which, metrologically, is manifested as an approximately ohmic conductivity. The immobilization of capture molecules in principle influences the material conversion at the electrode surface since the electrode is partially covered thereby, and on account of specific electrical properties of the molecules (for example on account of the fact that DNA molecules are often present as polyanions). This makes it more difficult for the detected sensor signals to be evaluated metrologically. Therefore, it is attempted to configure the measurement in such a way that only the value of the electrode capacitance $C_E$ that is dependent on the hybridization in the equivalent circuit diagrams specified is determined. As an alternative, it is possible to measure magnitude and phase of the impedance as a function of the exciting frequency, so that ideally all parameters can be determined from the resulting Bode diagram. However, this procedure is very complicated.

One possibility for obtaining signals that can be evaluated in an improved manner consists in the use of a so-called lock-in amplifier for detecting the sensor signal. This principle is explained below on the basis of the equivalent circuit diagrams 900, 1000 shown in FIG. 9, FIG. 10.

With the aid of a lock-in measuring device, an AC voltage $V_{char}$ with a frequency f is applied to the electrolyte 804 via the counterelectrode 803 which ensures a low-impedance connection to the electrolyte 804. It is then possible to measure the imaginary part and the real part of the complex total current $I_{meas}$ resulting from the elements $C_M$, $R_M$, $C_E$ and $R_E$.

Assuming that the magnitude of the complex impedance component of the electrolyte 804, namely $1/(2\pi f C_E)$, is significantly greater than the magnitude of the purely resistive component $R_E$, the measured current results as:

$$I_{meas} = V_{char} \times \cfrac{1}{R_E + \cfrac{R_M \times \frac{1}{j2\pi f C_M}}{R_M + \frac{1}{j2\pi f C_M}}} \quad (1)$$

The imaginary part of the current amounts to:

$$\text{Im}(I_{meas}) = V_{char} \times \frac{2\pi f C_M}{\left(\frac{R_E}{R_M} + 1\right)^2 + 4\pi^2 f^2 C_M^2 R_E^2} \quad (2)$$

Under the further assumption that the nonreactive resistance of the electrolyte $R_E$ is significantly less than the reciprocal of the parasitic sensor parallel conductance $R_M$, that is to say if $R_M \gg R_E$ holds true, and assuming that the frequency $f$ is chosen to be sufficiently low, so that $$4\pi^2 f^2 C_M^2 R_E^2 \ll 1 \quad (3)$$

is satisfied, then to an approximation the simple relationship $$\text{Im}(I_{meas}) = V_{char} \times 2\pi f C_M \quad (4)$$

can be specified for equation (2). Equation (4) clearly states that the imaginary part of the current that is determined by means of the lock-in method depends linearly on the sensor capacitance $C_M$.

It is only under these conditions that the precise change of $C_M$ comprises the information sought.

The need to satisfy equation (3) sufficiently well upwardly limits the choice of measurement frequency. However, the free choice of a frequency that is not all that low is desirable since in accordance with equation (4) the magnitude of the measurement signal to be evaluated rises proportionally with the frequency. In order to obtain a signal that can be evaluated well in accordance with equation (4) even in the case of the low frequencies and the stipulations for the order of magnitude of the voltage $V_{char}$, it is necessary to use either large-area sensors, which lead to large values for the sensor capacitance $C_M$, or highly sensitive amplifiers, which is complicated.

WO 01/42508 A2 discloses the detection of molecular interactions between biological molecules using electronic methods such as AC impedance measurement.

WO 96/33403 A1 discloses a sensor for an analyte with a working electrode arrangement having a microelectrode arrangement. Each microelectrode is provided with a layer of a redox-state-dependent conductive organic polymer.

WO 98/57157 A1 discloses a method for identifying and/or analyzing biological substances contained in a conductive solution.

SUMMARY OF THE INVENTION

The invention is based on the problem of providing a sensor arrangement in accordance with the impedance method, in the case of which sensor arrangement even signals with small amplitudes can be detected and evaluated sufficiently reliably, and in the case of which sensor arrangement the use of a label is dispensable.

The sensor arrangement according to the invention in accordance with a first aspect of the invention has a substrate and at least three sensor electrodes on the substrate, it being possible for capture molecules to be immobilized on at least a portion of the sensor electrodes, said capture molecules being set up in such a way that particles to be detected can hybridize with them. Furthermore, the sensor electrodes are arranged on the substrate in such a way that, in an operating state in which an electrically conductive substance is introduced into the sensor arrangement, the sensor electrodes are coupled to one another by means of the electrically conductive substance. Furthermore, the sensor arrangement contains a control circuit, which is set up in such a way that it can be used to apply a first electrical signal to a selected sensor electrode and simultaneously to apply a second electrical signal to at least two of the other sensor electrodes, the first electrical signal being a first temporally variable electrical signal and/or the second electrical signal being a second temporally variable electrical signal. The sensor arrangement furthermore contains a detection device, which is set up in such a way that, in a first operating state, in which a reference liquid is introduced into the sensor arrangement, a reference value of a third temporally variable electrical signal resulting from the first temporally variable electrical signal and/or from the second temporally variable electrical signal is detected at the selected sensor electrode. In a second operating state, in which an analyte possibly having particles to be detected is introduced into the sensor arrangement, a sensor value of a third temporally variable electrical signal resulting from the first temporally variable electrical signal and/or from the second temporally variable electrical signal is detected at the selected sensor electrode. An evaluation circuit of the sensor arrangement is set up in such a way that, on the basis of the reference value and the sensor value, it determines whether a hybridization event has taken place at the selected sensor electrode.

Furthermore, the invention provides a method for operating a sensor arrangement having the abovementioned features. In accordance with the method, a first electrical signal is applied to a selected sensor electrode and a second electrical signal is simultaneously applied to at least two of the other sensor electrodes, the first electrical signal being a first temporally variable electrical signal and/or the second electrical signal being a second temporally variable electrical signal. In a first operating state, in which a reference liquid is introduced into the sensor arrangement, a reference value of a third temporally variable electrical signal resulting from the first temporally variable electrical signal and/or from the second temporally variable electrical signal is detected at the selected sensor electrode. Furthermore, in a second operating state, in which an analyte possibly having particles to be detected is introduced into the sensor arrangement, a sensor value of a third temporally variable electrical signal of a selected sensor electrode resulting from the first temporally variable electrical signal and/or from the second temporally variable electrical signal is detected. Moreover, on the basis of the reference value and the sensor value, it is determined whether a hybridization event has taken place at the selected sensor electrode.

BRIEF DESCRIPTION OF THE DRAWINGS

Exemplary embodiments of the invention are illustrated in the figures and are explained in more detail below.

In the figures:

FIG. 1 shows a sensor arrangement in accordance with the prior art;

FIGS. 2A to 2F show cross-sectional views of a partial region of the sensor arrangement shown in FIG. 1 at different points in time during a method for operating the sensor arrangement;

FIGS. 3A, 3B show a plan view and a cross-sectional view along the section line I-I' of an interdigital electrode arrangement in accordance with the prior art;

FIGS. 4A, 4B show cross-sectional views of a first partial region of the interdigital electrode arrangement shown in FIG. 3 at different points in time during a method for operating the interdigital electrode arrangement in accordance with the prior art;

FIG. 5 shows a cross-sectional view of a second partial region of the interdigital electrode arrangement in accordance with the prior art as shown in FIG. 3;

FIG. 6 shows an equivalent circuit diagram of the first partial region of the interdigital electrode arrangement from FIG. 3 in accordance with the prior art;

FIGS. 7A, 7B show equivalent circuit diagrams of the first partial region of the interdigital electrode arrangement in accordance with the prior art as shown in FIG. 3;

FIGS. 8A, 8B show a plan view and a cross-sectional view along the section line II-II' of a sensor arrangement with reference electrode in accordance with the prior art;

FIG. 9 shows an equivalent circuit diagram of the sensor arrangement from FIG. 8 in accordance with the prior art;

FIG. 10 shows another equivalent circuit diagram of the sensor arrangement from FIG. 8 in accordance with the prior art;

FIG. 11 shows a diagrammatic cross-sectional view of a sensor arrangement in accordance with a first exemplary embodiment of the invention;

DETAILED DESCRIPTION OF PREFERRED EMBODIMENTS OF THE INVENTION

Figure 12:
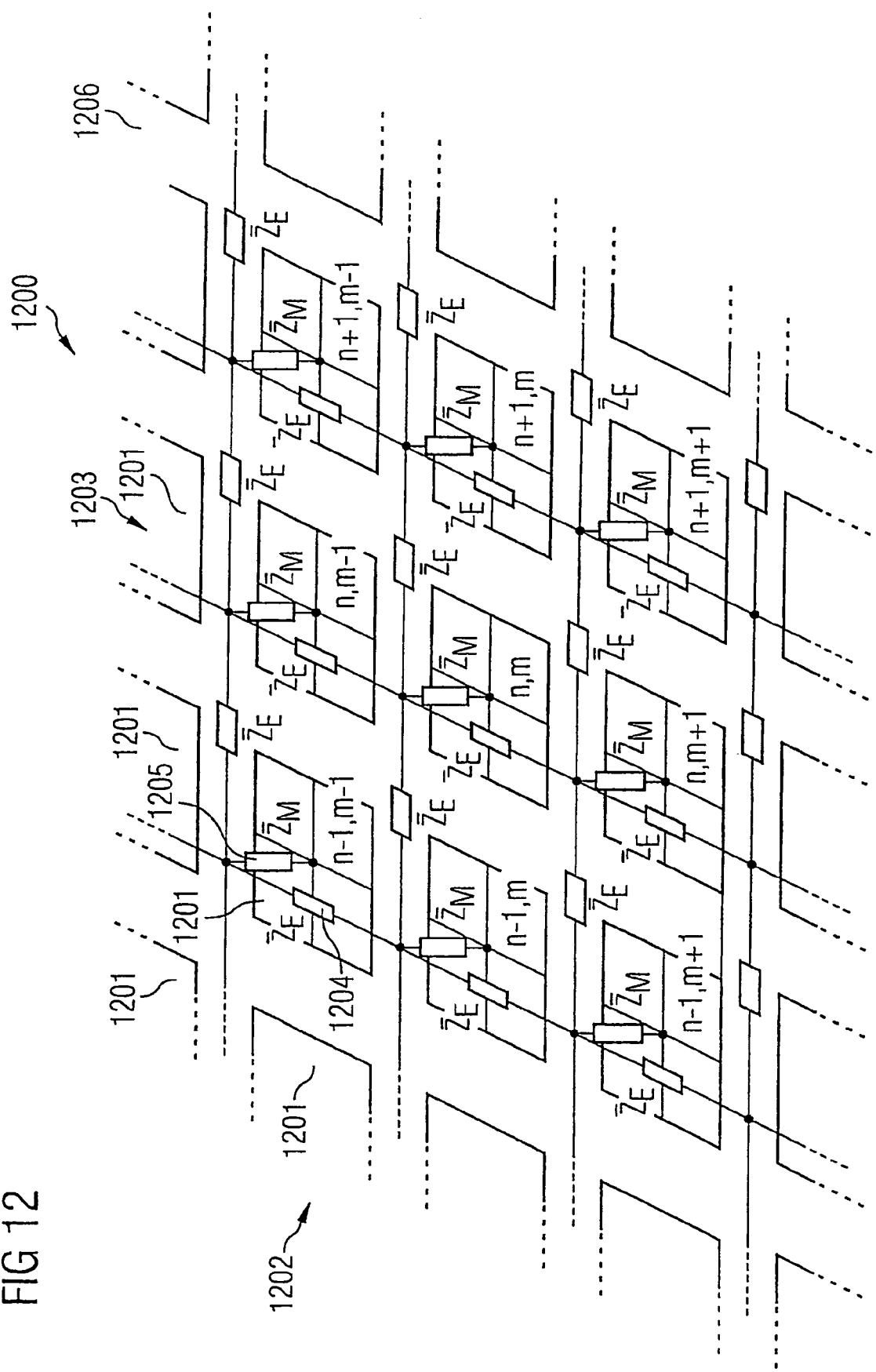
FIG. 12 shows a perspective diagrammatic view of a sensor arrangement in accordance with a second exemplary embodiment of the invention.

A basic idea of the invention is to be seen in the fact that a sensor arrangement having a multiplicity of sensor electrodes is provided on a substrate. Before and after a sensor event that possibly takes place (for example a hybridization between capture molecules and DNA half strands situated in an analyte), an electrical AC signal (for example an AC voltage or an AC current) is applied to a selected one of the electrodes, and a second AC signal (an electric current or an electrical voltage) resulting from the first AC signal is detected. Since the value of the impedance, in particular the value of the capacitance, between the selected sensor electrode and at least a portion of the other sensor electrodes changes characteristically owing to a sensor event, the occurrence of a hybridization event or some other sensor event can be deduced from the alteration of the second AC signal. At least two of the non-selected sensor electrodes are brought to an electrical reference potential.

As an alternative to a constant reference potential, a signal that is in antiphase with respect to the potential of the selected sensor electrode may also be applied to the other sensor electrodes.

Clearly, it is proposed to use an array configuration having a multiplicity of sensor electrodes, typical areas of the sensor electrodes lying in the range of from a few 100 $\mu m^2$ to a few 10 000 $\mu m^2$. Known capture molecules are applied and immobilized on the sensor electrodes in a position-specific manner, for example using microdispensing techniques. The use of a reference electrode, as described above with reference to FIG. 8A to FIG. 10, is avoided according to the invention. Consequently, the need for a special, problematic electrode material for such a reference electrode is also obviated.

In order to characterize the state of a specific sensor electrode, an AC voltage is preferably applied to this selected sensor electrode, and an AC current resulting from the AC voltage is detected at this sensor electrode. An electrical ground potential or a reference voltage is applied to at least two of the other electrodes. The reference voltage used may be the DC voltage average value of the AC voltage applied to the selected sensor electrode, that is to say the temporally averaged value of the AC voltage.

Clearly, the invention creates a novel array architecture, a new driving and a new possibility for evaluation of the sensor electrodes.

The realization of such arrays on a semiconductor chip as a substrate affords the advantage that it is possible to realize a sensor arrangement with a significantly higher number of individual sensor electrodes in conjunction with a reduced area. This advantage resides on the one hand in the significantly higher number of tests that can be implemented temporally in parallel by means of such a sensor arrangement and on the other hand in the significantly higher number of parameters that can be characterized in parallel. Furthermore, it is possible to reduce the volume of chemical reagents required for the operation of such sensor arrangements. In the case of biochemical applications, in particular, the chemical reagents are a very important cost factor, whereby the operating costs are reduced.

A further advantage is that it is possible to use a significantly smaller area for the sensor electrodes, compared with the electrode configurations in accordance with the prior art. The smaller signal amplitude on active semiconductor chips that is governed by the smaller sensor area of the individual sensors is not a disadvantage compared with a passive realization since, in an integrated sensor arrangement, this signal can be amplified "on-chip" with the aid of circuits that are integrated for example below the sensor electrodes in the substrate. Consequently, such chips are able to supply a better signal-to-noise ratio of the sensor signals to be evaluated. In particular, the tolerance of such chips in relation to interference signals coupled in externally is significantly greater than in the case of using passive electrical sensor arrays in which comparatively long electrical lines have to be coupled to the measuring equipment. Signals running on these lines are sensitive to interference coupling into the lines on account of their small amplitude.

A further advantage particularly in comparison with the reference electrode arrangement described with reference to FIG. 8 to FIG. 10 is that the technological requirements made of the materials to be used are much lower. In particular, the need to provide a reference electrode, which is often realized as a silver/silver chloride electrode, for producing an electrochemical reference potential with respect to the electrodes is avoided. Such a reference electrode is necessary particularly in the case of electrochemical sensors (e.g. redox recycling sensors), but not, on the other hand, in the case of impedance methods. This is a significant advantage for the realization of such sensor arrangements on active semiconductor chips (for example MOS chips) since the integration of new and additional materials into a semiconductor fabrication process is associated with high costs and high development outlay. For reasons of risk of contamination by such materials or else because the processing conditions of these materials are not compatible with the integrated circuit fabrication process (because they lead for example to damage to the—already produced previously in the process sequence—integrated components, electrical coupling means, and insulation layers), the integration of these materials is ruled out in principle.

One advantage of the sensor arrangement according to the invention in particular over the interdigital electrode arrangement of FIG. 3A, FIG. 3B is that the sensor electrodes of the sensor arrangement according to the invention, given the same overall area, supply a significantly larger signal than the configuration with the interdigital electrodes. This is due to the fact that the entire sensor area can be used as active electrode area. However, this also means contrariwise that the sensor area can be made smaller for a given requirement made of the amplitude of the sensor signal. This leads to a smaller area requirement for the circuit technology or to a higher performance of the driving circuits. Preferred developments of the invention emerge from the dependent claims.

The sensor arrangement may be set up for determining, for at least a portion of the sensor electrodes, sequentially in each case for a selected sensor electrode whether a hybridization event has taken place at the respectively selected sensor electrode. In other words, it is possible sequentially to select a plurality of sensor electrodes successively and to determine whether a sensor event has taken place at this sensor electrode.

The sensor arrangement may furthermore be set up for determining, for each selected sensor electrode, the quantity in which hybridization events have taken place at the selected sensor electrode. The sensor arrangement according to the invention can therefore be used both for qualitative and for quantitative analyses.

The sensor electrodes may be arranged essentially in matrix form on the surface of the substrate.

Furthermore, the sensor electrodes may be grouped or compartmentalized to form a plurality of sensor groups in such a way that each sensor group can optionally be operated separately from the other sensor groups or jointly with at least a portion of the other sensor groups. As a result, the invention makes it possible to use only a sufficiently large portion of the sensor electrodes for an analysis for which not all of the sensor electrodes provided on a sensor arrangement are required. Costs can thereby be saved.

The sensor electrode is preferably square, rectangular, circular, elliptical, honeycomb-shaped or octagonal. The sensor electrode may also be composed of a plurality of non-contiguous regions (clearly segments), the individual regions of a sensor electrode preferably being covered with and electrically coupled to the same capture molecules.

In particular, the sensor arrangement may be set up as an integrated circuit, as a result of which it is possible to utilize in particular the advantages of silicon microtechnology.

However, it must be emphasized that the sensor arrangements according to the invention need not necessarily be set up as an integrated circuit.

The substrate may be a semiconductor substrate (for example a silicon substrate, silicon wafer or silicon chip), a ceramic substrate, a glass substrate and a plastic substrate.

The first and/or the second temporally variable electrical signal may be a temporally variable electrical voltage and the third temporally variable electrical signal may be a temporally variable electric current. As an alternative, the first and/or the second temporally variable electrical signal may be a temporally variable electric current and the third temporally variable electrical signal may be a temporally variable electrical voltage.

The time dependence of the first and/or of the second temporally variable electrical signal and/or the time dependence of the third temporally variable electrical signal may be a mathematical sine function (or cosine function), a rectangular function, a sawtooth function, a triangular function, or a step function. What is important is that the first and/or the second temporally variable electrical signal is variable over time.

In the case of the sensor arrangement, the control circuit may be set up in such a way that the first electrical signal is a first temporally variable electrical signal and the second electrical signal is a constant reference potential. In other words, a temporally variable electrical signal (e.g. an AC voltage) may be applied to the selected sensor electrode, whereas a constant electrical potential may be applied to at least two of the other sensor electrodes.

As an alternative, in the case of the sensor arrangement, the control circuit may be set up in such a way that the second electrical signal is a second temporally variable electrical signal and the first electrical signal is a constant reference potential. In other words, a constant electrical potential may be applied to the selected sensor electrode, whereas a temporally variable electrical signal (e.g. an AC voltage) may be applied to at least two of the other sensor electrodes.

In accordance with a further alternative, the first electrical signal may be a first temporally variable electrical signal and the second electrical signal may be a second temporally variable electrical signal, the first and second temporally variable electrical signals being in antiphase with respect to one another. In this case, a respective AC voltage may be applied for example to all the sensor electrodes, the AC voltage at the selected sensor electrode being in antiphase with respect to the AC voltage at the other sensor electrodes (or at least a portion thereof).

The electrical reference potential may be the ground potential or a time average value of the first or of the second temporally variable electrical signal. If, by way of example, the time average value of the first temporally variable electrical signal (for example of a sinusoidal AC voltage) is used as the electrical reference potential of the non-selected sensor electrodes, then disturbing electrochemical conversions at electrodes (that is to say oxidation or reduction processes) are avoided. Owing to such oxidation or reduction processes, material may be deposited undesirably in a surrounding region of the sensor electrodes, the electrical properties of the sensor electrodes thereby being altered. The measurement may be adversely affected as a result.

In the case of the sensor arrangement, the reference liquid may be a different liquid than the analyte and be free of particles to be detected. Clearly, in accordance with this alternative, firstly a reference liquid free of particles to be detected is introduced into the sensor arrangement and the reference value of the third temporally variable electrical signal is detected. The analyte, i.e. a liquid to be examined which is different than the reference liquid, is then introduced into the sensor arrangement, thereby enabling hybridization events. Afterward, the sensor value of the third temporally variable electrical signal is detected.

As an alternative, the reference liquid may be the analyte, i.e. reference liquid and analyte may be one and the same liquid. In both operating states, this liquid is filled into the sensor arrangement. In this case, the sensor arrangement is set up in such a way that the first operating state is a first time period, in which essentially as yet no hybridization events have taken place and the second operating state is a second time period, temporally after the first time period, in which essentially all hybridization events have taken place.

Hybridization events take place in many cases with relatively long time constants, e.g. of the order of magnitude of hours. If an analyte is introduced into the sensor arrangement and the reference value of the third temporally variable electrical signal is detected immediately afterward, then clearly as yet no (or insignificantly few) hybridization events have taken place at this point in time. The sensor value of the third temporally variable electrical signal is detected after a predeterminable time period chosen such that possible hybridization events can proceed within said time period.

Furthermore the sensor arrangement may have an analog/digital converter circuit integrated in the substrate, said analog/digital converter circuit being set up in such a way that it converts an analog temporally variable electrical signal into a digital signal and provides it to the evaluation circuit. Furthermore, the sensor arrangement may be provided with an external supply unit, which is set up in such a way that it provides the control circuit with electrical voltage signals and/or electric current signals. Moreover, provision may be made of a digital/analog converter circuit integrated in the substrate, said digital/analog converter circuit being set up in such a way that it converts a digital voltage signal and/or current signal of the external supply unit into an analog signal and provides it to the control circuit. Furthermore, a selection circuit may be integrated in the substrate, said selection circuit being set up in such a way that it sequentially selects in each case one of the sensor electrodes. For this purpose, it is possible, by way of example, to provide an enable/disable input at voltage sources for generating the first temporally variable electrical signal, or it is possible for one of the sensor electrodes to be switched in or out using a transistor switch.

The sensor arrangement according to the invention is attractive particularly in connection with active silicon chips in which electrical circuits for driving the electrode, for measurement, conditioning and preprocessing of the sensor signal are arranged below each electrode. On such chips, it is furthermore possible to effect the driving of the chips and the transfer of the measurement data via a purely digital, i.e. error-robust, interface to external devices. The circuits provided on the chip may be e.g. analog/digital converters which convert the signal supplied in preamplified or preprocessed form by the sensor circuits into a digital signal. Furthermore, provision may be made of digital/analog converters which convert signals coded in digital form by external devices into analog signals required for the operation of the sensors (for example an AC voltage). Moreover, provision may be made of logic circuits which convert signals which are supplied in digital form by external devices and serve for the driving of the chip (for example for the selection of a position) into suitable chip-internal control signals. Such a configuration is advantageous since the driving of the sensors with analog signals and the transport of the sensitive analog measurement signals are not effected via long leads. As a result, the susceptibility of the chips to interference and the noise component in the measurement signal are considerably reduced since the sensitive analog signals do not have to leave the chip.

Furthermore, capture molecules may be immobilized on at least one of the sensor electrodes. In particular, different capture molecules may be immobilized on different sensor electrodes, so that an analyte can be tested for the presence of different particles to be detected.

The sensor arrangement may be set up in particular as a biosensor arrangement, more particularly as a DNA sensor arrangement.

The evaluation circuit may be set up in such a way that it determines, on the basis of the reference value and the sensor value of the third temporally variable electrical signal and on the basis of the first and/or second temporally variable electrical signal, the value of the impedance between the selected sensor electrode and an electrically conductive substance (i.e. in particular the reference liquid or the analyte) introduced into the sensor arrangement in the first operating state and in the second operating state. Since the reference liquid is introduced into the sensor arrangement in the first operating state, the value of the impedance between the selected sensor electrode and the reference liquid is determined in the first operating state. Since the analyte is introduced into the sensor arrangement in the second operating state, the value of the impedance between the selected sensor electrode (with the particles to be detected that have hybridized with the capture molecules at the sensor electrode) and the analyte is determined in the second operating state.

Furthermore, the evaluation circuit may be set up in such a way that it determines, on the basis of the reference value and the sensor value of the third temporally variable electrical signal and on the basis of the first and/or second temporally variable electrical signal, the value of the capacitance between the selected sensor electrode and an electrically conductive substance introduced into the sensor arrangement in the first operating state and in the second operating state. Many applications permit the approximation with good accuracy that the sensor impedance is dominated by the capacitive component, whereas the impedance of an electrolyte or a resistive component of the sensor impedance can often be disregarded.

The evaluation circuit may be set up in such a way that it determines, on the basis of the quotient of the values of the capacitance between the selected sensor electrode and an electrically conductive substance introduced into the sensor arrangement in the first operating state and in the second operating state, whether hybridization events have taken place at the selected sensor electrode and/or the quantity in which hybridization events have taken place at a selected sensor electrode.

As an alternative to the measure described last, the evaluation circuit may be set up in such a way that it determines, for at least a portion of the sensor electrodes, whether hybridization events have taken place at the respectively selected sensor electrode and/or the quantity in which hybridization events have taken place at the respectively selected sensor electrode, by determining the values $\beta(i,j)C_{array}(i,j)$ for the first and second operating states from the system of equations $$C_{meas}(n, m) = \beta(n, m)C_{array}(n, m) \times \left[ 1 - \frac{\beta(n, m)C_{array}(n, m)}{\sum_{x=1}^{N} \sum_{y=1}^{M} \beta(x, y)C_{array}(x, y)} \right]. \quad (5)$$

In equation (5), n,m are the indices of a selected sensor electrode in the cell array and x,y are indices of the sensor electrodes in the cell array. N*M is the number of sensor electrodes in the cell array (e.g. N rows and M columns of sensor electrodes are provided in a matrix-type cell array). Furthermore, $C_{array}(i,j)$ is the value of the capacitance between the sensor electrode having the indices i,j and the electrolyte. The non-selected sensor electrodes form further capacitances with respect to the electrolyte in the first operating state. Moreover, $\beta(i,j)C_{array}(i,j)$ is the value of the capacitance between the sensor electrode having the indices i,j and the electrolyte in the second operating state. The non-selected sensor electrodes form further capacitances with respect to the electrolyte in the second operating state. Furthermore, $C_{meas}(n,m)$ is the value of the capacitance determined, i.e. measured, between the selected sensor electrode having the indices n,m and the electrolyte (an electrically conductive substance introduced into the sensor arrangement). Clearly, equation (5) is solved numerically for the first and the second operating state, respectively, by solving a system of equations having in each case N×M equations and N×M unknowns, namely the products $\beta(n,m)C_{array}(n,m)$, for each operating state. Clearly, the values $\beta(n,m)$ contain the information about a sensor event that has possibly taken place.

The evaluation circuit may be set up in such a way that it uses the approximation N×M>>1 when determining the values $\beta(i,j)C_{array}(i,j)$. In other words, it is assumed here that a large number of sensor electrodes are provided in the sensor arrangement. Alternatively or supplementarily, the evaluation circuit may be set up in such a way that it uses the approximation $$\sum_{x=1}^{N} \sum_{y=1}^{M} \beta(x, y)C_{array}(x, y) \gg \beta(n, m)C_{array}(n, m) \quad (6)$$

for determining the values $\beta(i,j)C_{array}(i,j)$. This clearly corresponds to the assumption that the values of the respective capacitances differ from one another to a sufficiently small extent, i.e. not by orders of magnitude. Clearly, equation (5) can be considerably simplified using the two approximations described, which enables a numerically simpler evaluation in the evaluation circuit.

A sensor arrangement according to the invention in accordance with a second aspect of the invention is described below. The refinements of the sensor arrangement in accordance with the first aspect of the invention also hold true for the sensor arrangement in accordance with the second aspect of the invention.

The second aspect of the invention provides a sensor arrangement having a substrate and having at least three sensor electrodes on the substrate. Capture molecules are immobilized on at least a portion of the sensor electrodes, said capture molecules being set up in such a way that particles to be detected can hybridize with them. At least one reference sensor electrode is free of such capture molecules which are set up in such a way that particles to be detected can hybridize with them. In other words, capture molecules can also be immobilized on the reference sensor electrode (e.g. double-stranded DNA), but not such capture molecules which can hybridize with other particles. However, the reference sensor electrode may also be completely free of capture molecules. The sensor electrodes are arranged on the substrate in such a way that, in an operating state in which an electrically conductive substance is introduced into the sensor arrangement, the sensor electrodes are coupled to one another by means of the electrically conductive substance. A control circuit is set up in such a way that it can be used to apply a first electrical signal to a selected sensor electrode and to the reference sensor electrode and simultaneously to apply a second electrical signal to at least one of the other sensor electrodes, the first electrical signal being a first temporally variable electrical signal and/or the second electrical signal being a second temporally variable electrical signal. A detection device is set up in such a way that, in an operating state in which an analyte possibly having particles to be detected is introduced into the sensor arrangement, a reference value of a third temporally variable electrical signal resulting from the first temporally variable electrical signal and/or from the second temporally variable electrical signal is detected at the reference sensor electrode. Furthermore, a sensor value of a third temporally variable electrical signal resulting from the first temporally variable electrical signal and/or from the second temporally variable electrical signal is detected at the selected sensor electrode by means of the detection device. An evaluation circuit is set up in such a way that, on the basis of the reference value and the sensor value, it determines whether a hybridization event has taken place at the selected sensor electrode.

In accordance with the second aspect of the invention, clearly, by way of example, an AC voltage is applied to the reference sensor electrode and to the selected sensor electrode. Since capture molecules with which particles of an analyte to be detected can hybridize are indeed immobilized at the selected sensor electrode, but not at the reference sensor electrode, the sensor value changes owing to a hybridization event, whereas the reference value of an AC current resulting from the AC voltage does not change.

In accordance with this aspect of the invention, the reference sensor electrode may be free of capture molecules or such capture molecules which cannot hybridize with particles to be detected (e.g. double-stranded DNA) may be immobilized on the reference sensor electrode.

The method according to the invention for operating the sensor arrangement according to the invention is described in more detail below. Refinements of the sensor arrangement also hold true for the method for operating the sensor arrangement.

What may be used as reference liquid is essentially the same substance as for the analyte, apart from the fact that the reference liquid is free of particles to be detected.

By virtue of the fact that the reference liquid differs from the analyte essentially only by the particles to be detected, which are usually present in a low concentration, it is ensured that the electrical properties at the sensor electrodes are not influenced by overly different reference liquid and analyte liquid. The measurement accuracy is thereby increased.

It should be noted that a selected sensor electrode can clearly be operated in antiphase with respect to the non-selected sensor electrodes. That is to say that, by way of example, a first AC voltage can be applied to the selected sensor electrode, and that a second AC voltage can simultaneously be applied to at least a portion of the other sensor electrodes. The first AC voltage is then preferably in antiphase with respect to the second AC voltage. As an alternative, by way of example, a first AC current can be applied to the selected sensor electrode, and a second AC current can simultaneously be applied to at least a portion of the other sensor electrodes. The first AC current is then preferably in antiphase with respect to the second AC current.

Furthermore, it should be noted that, according to the invention, after the hybridization event that has taken place, the sensor arrangement can be rinsed by removing the analyte and by introducing a rinsing solution that is set up in such a way that unchanged single-stranded capture molecules that have not hybridized are thereby stripped away from the sensor electrodes, whereas capture molecules that have hybridized with particles to be detected are not stripped away by the rinsing solution.

What are described in the context of this description are predominantly DNA sensor arrangements for detecting and ascertaining DNA strands, which represent an important class and an important field of application of such sensor arrays. However, the principle of the sensor arrangements described is not restricted to the area of DNA sensor technology, but rather applies generally to any desired sensor class.

Clearly, the invention creates a possibility of providing and operating a simplified and highly accurate sensor arrangement using the impedance method.

A description is given below, with reference to FIG. 11, of a sensor arrangement 1100 in accordance with a first preferred exemplary embodiment of the invention.

The sensor arrangement 1100 has a silicon substrate 1101 and also a first sensor electrode 1102, a second sensor electrode 1103 and a third sensor electrode 1104, in each case made of gold material, which are arranged on the substrate 1101. First capture molecules 1105 are immobilized on the first sensor electrode 1102. Second capture molecules 1106 are immobilized on the second sensor electrode 1103. Third capture molecules 1107 are immobilized on the third sensor electrode 1104. Each of the types of capture molecules 1105 to 1107 is set up in such a way that in each case particles that are to be specifically detected can hybridize with them.

In accordance with the operating state of the sensor arrangement 1100 as shown in FIG. 11, an analyte 1109 with DNA half strands 1108 to be detected is introduced into the sensor arrangement 1100. the DNA half strands 1108 to be detected are complementary to the first capture molecules 1105, for which reason the first capture molecules 1105 hybridize with the DNA half strands 1108 to be detected. By contrast, the base sequence of the second and third capture molecules 1106, 1107 is not complementary to the DNA half strands 1108 to be detected, so that no hybridization events take place at the second electrode 1103 and at the third electrode 1104.

As shown in FIG. 11, the sensor electrodes 1102 to 1104 are arranged on the substrate in such a way that, in an operating state in which the electrolytic analyte 1109 is introduced into the sensor arrangement 1100 as an electrically conductive substance, the sensor electrodes 1102 to 1104 are electrically coupled by means of the electrically conductive electrolyte solution 1109. A container 1110 on the substrate 1101 enables the analyte 1109 to be filled into the sensor arrangement 1100.

Furthermore, FIG. 11 shows a control circuit 1111, which is set up in such a way that it can be used to apply a sinusoidal and therefore temporally variable AC voltage to a respectively selected sensor electrode 1102 to 1104. This is realized by means of the first to third AC voltage sources 1113 to 1115. By means of a first control line 1112a, a control unit 1112 of the control circuit 1111 is coupled to the first AC voltage source 1113, it being possible for the first AC voltage source 1113 to be activated (or deactivated) by means of a signal from the control unit 1112 via the first control line 1112a. In accordance with the operating state of the sensor arrangement 1100 as shown in FIG. 11, the first sensor electrode 1102 is activated, whereas the second and third sensor electrodes 1103 and 1104 are deactivated. Consequently, the control unit 1112 provides the first AC voltage source 1113 with a signal such that the first AC voltage source 1113 is activated. Moreover, the control unit 1112, via the second control line 1112b, provides the second AC voltage source 1114 with a signal such that the second AC voltage source 1114 is deactivated and no AC voltage is present at the second sensor electrode 1103. The third AC voltage source 1115 is also deactivated since the control unit 1112 communicates a corresponding control signal to the third AC voltage source 1115 via the third control line 1112c. As a result, in accordance with the operating state shown in FIG. 11, the first AC voltage source 1113 supplies the first sensor electrode 1102 with an electrical AC voltage with a sinusoidal signal profile, whereas the second and third sensor electrodes 1103, 1104 are at electrical ground potential 1121 as reference potential.

Furthermore, the sensor arrangement 1100 is provided with a detection device 1116 containing a first current detection unit 1117 for detecting an electric current of the first sensor electrode 1102, a second current detection unit 1118 for detecting an electric current of the second sensor electrode 1103 and also a third current detection unit 1119 for detecting an electric current of the third sensor electrode 1104. The current detection units 1117 to 1119 may be configured as ammeters, for example. The detection device 1116 is set up in such a way that, in a first operating state (not shown), in which a reference liquid (not shown) free of particles 1108 to be detected is introduced into the sensor arrangement 1100, an electric reference current resulting from the AC voltage applied to the selected sensor electrode 1102 by means of the first AC voltage source 1113 is detected by means of the first current detection unit 1117. In other words, in accordance with this first operating state, an electrolyte reference liquid having no particles to be detected is filled into the sensor arrangement 1100 instead of the analyte 1109. The same material as for the analyte 1109 is used for the reference liquid, however, apart from the fact that the reference liquid is free of particles 1108 to be detected. Furthermore, the detection device 1116 is set up in such a way that, in the second operating state shown in FIG. 11, in which an analyte 1109 having DNA half strands 1108 to be detected is introduced into the sensor arrangement 1100, an electric sensor current is detected, which results from the electrical AC voltage applied to the first sensor electrode 1102 by means of the first AC voltage source 1113.

Furthermore, an evaluation circuit 1120 is integrated in the substrate 1101 in the case of the sensor arrangement 1100, which evaluation circuit is set up in such a way that, on the basis of the electric reference current and the electric sensor current, it determines whether a hybridization event has taken place at the selected sensor electrode 1102. For this purpose, the evaluation circuit 1120 is provided with the electric current values detected by the current detection units 1117 to 1119 by means of first to third coupling lines 1120a to 1120c.

In accordance with the exemplary embodiment described, the procedure of determining the reference current and the sensor current is carried out for each of the sensor electrodes 1102 to 1104 successively for the first and second operating states by sequentially selecting the sensor electrodes 1102 to 1104. The evaluation circuit 1120 is set up in such a way that, on the basis of the detected electric reference and sensor currents and on the basis of the AC voltages applied by means of the respective AC voltage sources 1113 to 1115, it determines the value of the impedance between the respectively selected sensor electrode (the first sensor electrode 1102 in accordance with FIG. 11) and the analyte 1109, to be precise in the first operating state (not shown) and in the second operating state (shown in FIG. 11).

Clearly, the value of the impedance between the selected sensor electrode 1102 and the analyte 1109 changes owing to a sensor event, that is to say a hybridization between first capture molecules 1105 and DNA half strands 1108 to be detected on the first sensor electrode 1102. This is clearly attributable to the fact that, on account of the hybridization event, electrolyte liquid with good electrical conductivity is displaced from a surrounding region of the selected sensor electrode 1102 and is replaced by DNA material 1108 with different electrical properties than the electrolyte 1109. As a result, the value of the impedance changes, which, for an AC voltage remaining the same, provided by the first AC voltage source 1113, leads to different values of the current intensities that are detected by the first current detection unit 1117 in the first and in the second operating state, respectively. The alteration of the impedance and therefore the quantity of hybridization events that have taken place on the first sensor electrode 1102 can be deduced from said altered current intensity. Therefore, the alteration of the impedance is a measure of the concentration of DNA half strands 1108 in the analyte 1109, so that the value of the concentration can be determined.

In the case of the sensor arrangement 1100, clearly one and the same sensor electrode functions as selected sensor electrode or as counterelectrode in different operating states.

A description is given below, with reference to FIG. 12, of a sensor arrangement 1200 in accordance with a second exemplary embodiment of the invention.

The sensor arrangement 1200 has a multiplicity of sensor electrodes 1201 arranged in matrix form (along rows 1202 and columns 1203) on a substrate 1206. The diagrammatic perspective view of FIG. 12 shows how an electrolyte filled into the sensor arrangement 1200 has an effect in terms of circuitry. If an electrolyte is filled into the sensor arrangement 1200, then the various sensor electrodes 1201 are coupled to one another by means of the electrolyte. The electrolyte may be assigned an impedance $Z_E$ in terms of circuitry. This electrolyte impedance 1204 is provided pairwise between in each case two sensor electrodes 1201, as shown in FIG. 12. Furthermore, each sensor electrode 1201 is assigned an impedance $Z_M$ in terms of circuitry, which in FIG. 12 is characterized in that a sensor impedance 1205 is provided for each sensor electrode 1201. As is furthermore shown in FIG. 12, a first index i (column index) and a second index j (row index) are assigned to each sensor electrode 1201 in the matrix-type arrangement, FIG. 12 showing the first index with the values n−1, n, n+1 and the second index with the values m−1, m+1.

For the characterization of a specific position of sensor electrodes 1201, an AC voltage is applied at the selected position and the measurement current is measured there (as an alternative, an AC current is applied and a resulting AC voltage is measured), whereas all the other sensor electrodes 1201 are brought to the ground potential.

Figure 13:
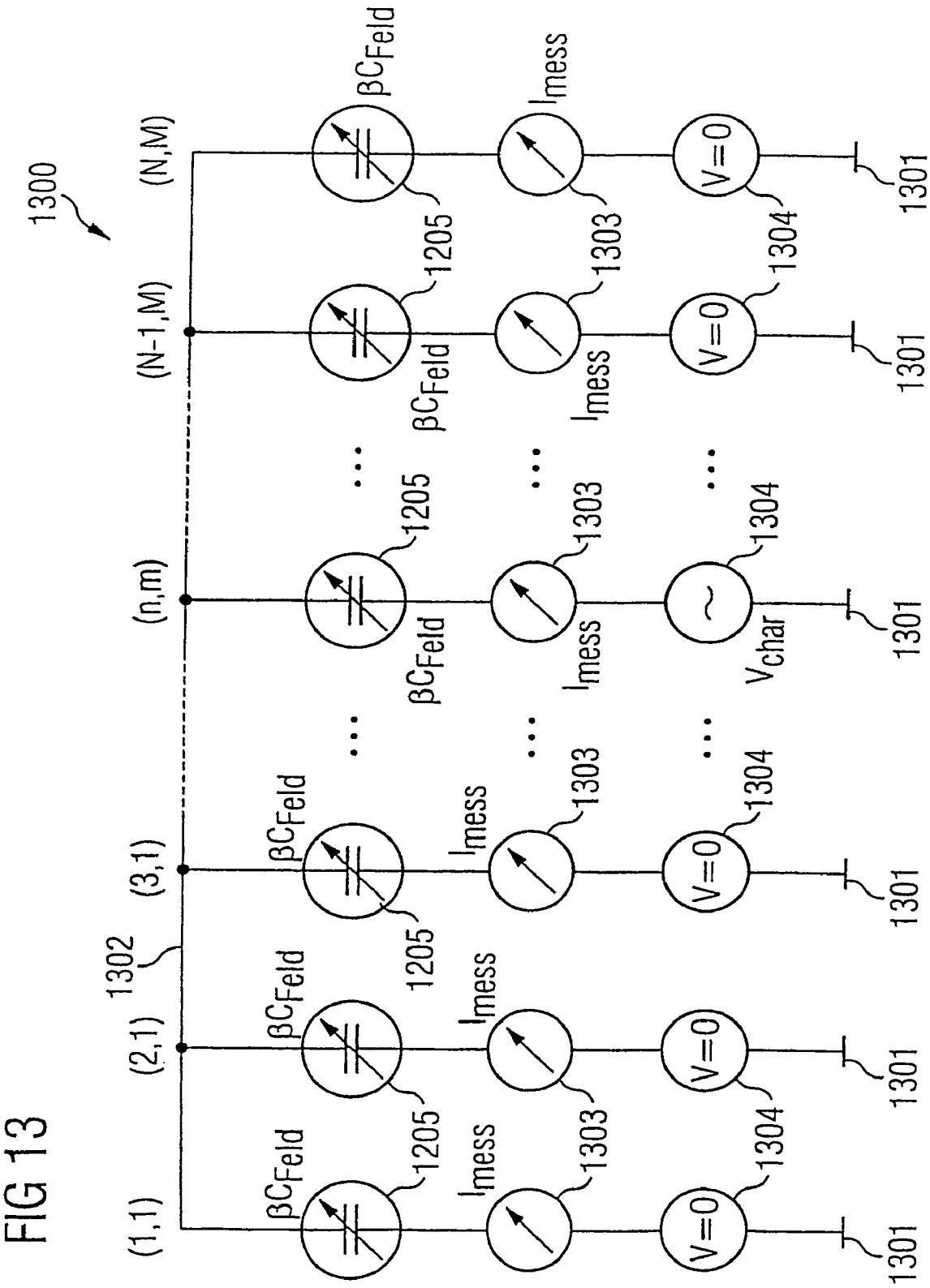
FIG. 13 shows an equivalent circuit diagram of the sensor arrangement in accordance with the second exemplary embodiment of the invention as shown in FIG. 12.

FIG. 13 shows a diagrammatic equivalent circuit diagram 1300 of the sensor arrangement 1200.

In FIG. 13, the electrolye impedance 1204 $Z_E$ is disregarded in comparison with the often significantly greater sensor impedance 1205 $Z_M$. FIG. 13 illustrates the N×M sensor arrays arranged one beside the other, different sensor electrodes 1201 being coupled by means of a global coupling means 1302 (clearly the electrically conductive electrolyte). In FIG. 13, the sensor impedance 1205 $Z_M$ is approximated by its often predominant capacitive component $\beta C_{array}$, i.e. the resistive component is disregarded. There is a current detection device 1303 for detecting an electric current in each case below each sensor electrode 1201, that is to say coupled to the sensor impedance 1205 $Z_M$.

Furthermore, each sensor electrode 1201 is assigned an AC voltage source 1304. Each of the AC voltage sources 1304 can be selected separately by means of an enable/disable input (not shown in FIG. 13) of each AC voltage source 1304. In other words, an electrical AC voltage $V_{char}$ is applied to this selected AC voltage source 1304, whereas all the other AC voltage sources 1304 are brought to the electrical potential V=0 volts. In accordance with the scenario shown in FIG. 13, the sensor electrode 1201 having the indices (n,m) is selected, for which reason an electrical AC voltage $V_{char}$ is applied to the associated sensor electrode 1201 by means of the associated AC voltage source 1304.

Figure 14:
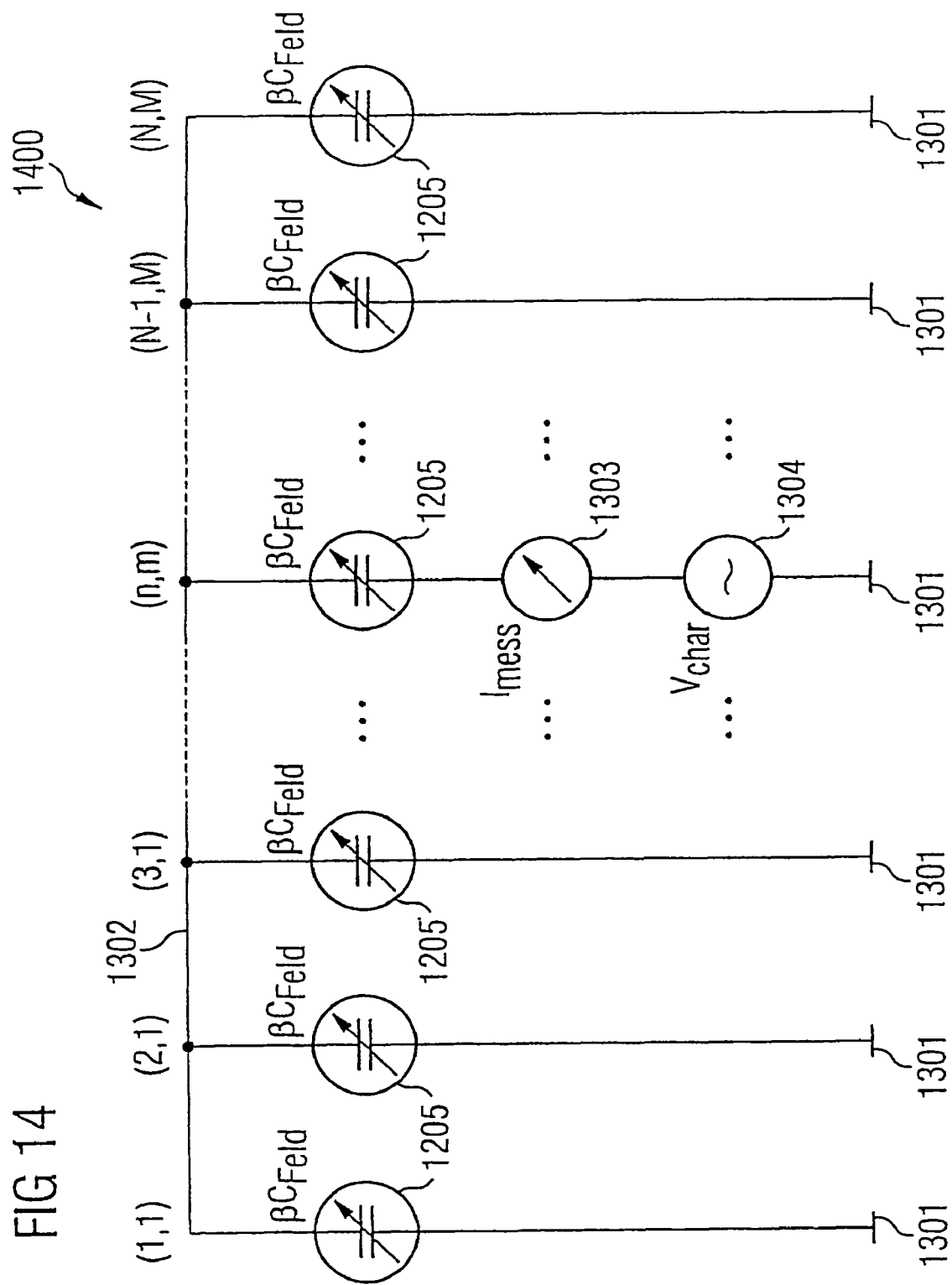
FIG. 14 shows another equivalent circuit diagram of the sensor arrangement in accordance with the second exemplary embodiment of the invention as shown in FIG. 12.

FIG. 14 shows another equivalent circuit diagram 1400 of the sensor arrangement 1200.

In accordance with the operating state shown in FIG. 13, FIG. 14, by means of the AC voltage source 1304, an electrical AC voltage is applied to the sensor electrode 1201 having the indices n,m by means of the AC voltage source 1304, and a measurement current $I_{meas}$ can be detected by means of the current detection device 1303.

In the case of the configuration shown in FIG. 14, in the case of the series circuit comprising the capacitance of the selected sensor electrode 1201 (n,m) with the summation circuit of the capacitances of all the non-selected sensor electrodes 1201, the following is measured:

$$C_{meas}(n, m) = \frac{\beta(n, m)C_{array}(n, m) \times \left(\left[\sum_{x=1}^{N}\sum_{y=1}^{M} \beta(x, y)C_{array}(x, y)\right] - \beta(n, m)C_{array}(n, m)\right)}{\beta(n, m)C_{array}(n, m) + \left(\left[\sum_{x=1}^{N}\sum_{y=1}^{M} \beta(x, y)C_{array}(x, y)\right] - \beta(n, m)C_{array}(n, m)\right)} \quad (7a)$$

$$= \beta(n, m)C_{array}(n, m) \times \frac{\left(\left[\sum_{x=1}^{N}\sum_{y=1}^{M} \beta(x, y)C_{array}(x, y)\right] - \beta(n, m)C_{array}(n.m)\right)}{\sum_{x=1}^{N}\sum_{y=1}^{M} \beta(x, y)C_{array}(x, y)} \quad (7b)$$

$$= \beta(n, m)C_{array}(n, m) \times \left[1 - \frac{\beta(n, m)C_{array}(n, m)}{\sum_{x=1}^{N}\sum_{y=1}^{M} \beta(x, y)C_{array}(x, y)}\right]. \quad (7c)$$

In equations (7a), (7b), (7c), $C_{array}(x,y)$ denotes the electrode capacitance of the sensor electrode 1201 having the coordinates (x,y) temporally before the hybridization (first operating state), $\beta(x,y)C_{array}(x,y)$ denotes the electrode capacitance of the sensor electrode 1201 of the position (x,y) temporally after hybridization (second operating state), and $\beta(x,y)$ denotes the change in the capacitance of a position (x,y) brought about by means of the hybridization. Equations (7a) to (7c) hold true before and after the hybridization, that is to say in the first and second operating states, $\beta(x,y)=1$ holding true before the hybridization. $\beta(x,y) \neq 1$ holds true after a hybridization event.

Consequently, determining the parameter β(x,y) for all positions (x,y) is the aim of the evaluation in accordance with the exemplary embodiment described.

The following holds true for arrays having a not overly small number of positions:

$$M \times N \gg 1 \tag{8}$$

If the respective values of the capacitances $C_{array}(x,y)$ and $\beta(x,y)C_{array}(x,y)$ do not differ from one another by orders of magnitude, something which is often fulfilled to a good approximation, the following also holds true:

$$\sum_{x=1}^{N}\sum_{y=1}^{M} \beta(x,y)C_{array}(x,y) \gg \beta(n,m)C_{array}(n,m). \tag{9}$$

With the approximation from equation (9), there follows from equation (7c) to a good approximation:

$$C_{meas}(n,m) \approx \beta(n,m) C_{array}(n,m) \tag{10}.$$

Using the detected measured values for $C_{meas}(n,m)$ before the hybridization (first operating state) and after the hybridization (second operating state), the result is:

$$\beta(n,m) = \frac{C_{meas}(n,m)|_{after\ hybridization\ phase}}{C_{meas}(n,m)|_{before\ hybridization\ phase}}. \tag{11}$$

For the case where a particularly high accuracy is desired or where an array under consideration has such a small number of sensor arrays that the approximation of equation (8) is only fulfilled moderately well, the system of equations given by equations (7a) to (7c) can also be solved exactly (numerically). Equations (7a) to (7c) yield, for the operating states before and after the hybridization phase, in each case a set of M×N equations for the M×N values to be determined β(X,y) $C_{array}(x,y)$ where x=1, 2, ..., N and y=1, 2, ..., M.

A description is given below, with reference to FIG. 15, of a sensor arrangement 1500 in accordance with a third exemplary embodiment of the invention.

The sensor arrangement 1500 contains a substrate 1501 and three sensor electrodes 1502 to 1504 on the substrate 1501. First capture molecules 1505 are immobilized on a first sensor electrode 1502, said capture molecules being set up in such a way that particles 1508 of an analyte 1509 to be detected can hybridize with them. Second capture molecules 1506 are immobilized on a second sensor electrode 1503. A reference sensor electrode 1504 is free of capture molecules. The sensor electrodes 1502 to 1504 are arranged on the substrate 1501 in such a way that, in an operating state in which an electrically conductive substance such as the analyte 1509 is introduced into the sensor arrangement 1500, the sensor electrodes 1502 to 1504 are coupled to one another by means of the electrically conductive substance. A control circuit 1507 is set up in such a way that it can be used to apply an AC voltage to a selected sensor electrode, the first sensor electrode 1502 in accordance with the scenario shown in FIG. 15, and to the reference sensor electrode 1504 and simultaneously to apply the electrical ground potential to the second sensor electrode 1503. A detection device 1510 is set up in such a way that, in an operating state in which the analyte 1509 having particles 1508 to be detected is introduced into the sensor arrangement 1500, a reference value of an AC current resulting from the AC voltage is detected at the reference sensor electrode 1504. Furthermore, a sensor value of the AC current resulting from the AC voltage is detected at the selected sensor electrode 1502 by means of the detection device 1510. An evaluation circuit 1511 is set up in such a way that, on the basis of the reference value and the sensor value, it determines whether a hybridization event has taken place at the selected sensor electrode 1502.

Figure 15:
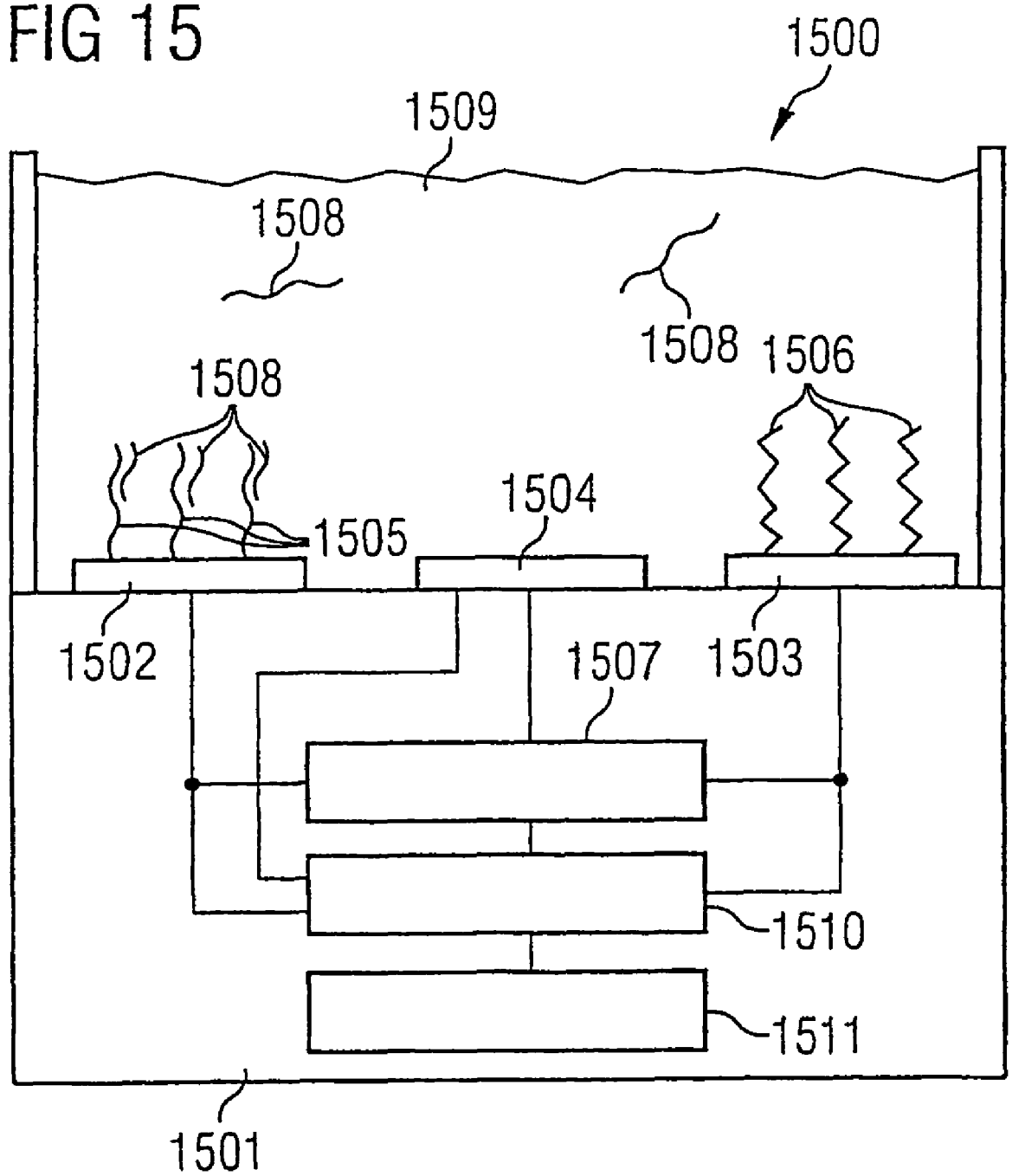
FIG. 15 shows a diagrammatic cross-sectional view of a sensor arrangement in accordance with a third exemplary embodiment of the invention.

Since, as shown in FIG. 15, capture molecules 1505 with which particles 1508 of the analyte 1509 to be detected can hybridize are indeed immobilized at the selected sensor electrode 1502, but not at the reference sensor electrode 1504, the sensor value changes significantly owing to a hybridization event, but not, on the other hand, the reference value of the AC current resulting from the AC voltage.

The invention claimed is:

1. A sensor arrangement, set up as an integrated circuit, comprising:
    a substrate;
    at least three sensor electrodes arranged on the substrate such that, in an operating state in which an electrically conductive substance is introduced into the sensor arrangement, the sensor electrodes are coupled to one another by means of the electrically conductive substance;
    capture molecules immobilized on at least a portion of the sensor electrodes, wherein molecules to be detected can hybridize with the capture molecules;
    a control circuit for applying a first electrical signal to a selected sensor electrode and simultaneously applying a second electrical signal to at least two of the other sensor electrodes, the first electrical signal being a first temporally variable electrical signal and/or the second electrical signal being a second temporally variable electrical signal;
    a detection device, which is set up such that,
        in a first operating state, in which a reference liquid is introduced into the sensor arrangement, a reference value of a third temporally variable electrical signal resulting from the first temporally variable electrical signal and/or from the second temporally variable electrical signal is detected at the selected sensor electrode; and
        in a second operating state, in which an analyte possibly having molecules to be detected is introduced into the sensor arrangement, a sensor value of the third temporally variable electrical signal resulting from the first temporally variable electrical signal and/or from the second temporally variable electrical signal is detected at the selected sensor electrode; and
    an evaluation circuit, which, on the basis of the reference value and the sensor value, determines whether a hybridization event has taken place at the selected sensor electrode,
    wherein the evaluation circuit determines, based on the reference value and the sensor value of the third temporally variable electrical signal and based on the first and/or second temporally variable electrical signal, the value of the capacitance between the selected sensor electrode and an electrically conductive substance introduced into the sensor arrangement in the first operating state and in the second operating state, and
    wherein the evaluation circuit determines, for at least a portion of the sensor electrodes, whether hybridization events have taken place at the selected sensor electrode and/or the quantity in which hybridization events have taken place at the selected sensor electrode, by determining the values $\beta(i,j)C_{array}(i,j)$ for the first and second operating states from the system of equations $$C_{meas}(n,m) = \beta(n,m)C_{array}(n,m) \times \left[1 - \frac{\beta(n,m)C_{array}(n,m)}{\sum_{x=1}^{N}\sum_{y=1}^{M}\beta(x,y)C_{array}(x,y)}\right]$$

where n,m are indices of a selected sensor electrode in the cell array;

where x,y are indices of the sensor electrodes in the cell array;

where N*M is the number of sensor electrodes in the cell array;

where $C_{array}(i,j)$ is the value of the capacitance between the sensor electrode having the indices i,j and the reference liquid in the first operating state;

where $\beta(i,j)C_{array}(i,j)$ is the value of the capacitance between the sensor electrode having the indices i,j and the analyte in the second operating state; and where $C_{meas}(n,m)$ is the value of the capacitance determined between the selected sensor electrode having the indices n,m and an electrically conductive substance introduced into the sensor arrangement.

2. The sensor arrangement as claimed in claim 1, which determines, for at least a portion of the sensor electrodes, sequentially in each case for a selected sensor electrode whether a hybridization event has taken place at the respectively selected sensor electrode.

3. The sensor arrangement as claimed in claim 2, which determines, for each selected sensor electrode, the quantity in which hybridization events have taken place at the selected sensor electrode.

4. The sensor arrangement as claimed in claim 1, wherein the sensor electrodes are arranged essentially in matrix form on the surface of the substrate.

5. The sensor arrangement as claimed in claim 1, wherein the sensor electrodes are grouped to form a plurality of sensor groups such that each sensor group can optionally be operated separately from the other sensor groups or jointly with at least a portion of the other sensor groups.

6. The sensor arrangement as claimed in claim 1, wherein at least one sensor electrode is square, rectangular, circular, elliptical, honeycomb-shaped, octagonal, or composed of a plurality of non-contiguous regions.

7. The sensor arrangement as claimed in claim 1, wherein the substrate is a ceramic substrate, a silicon substrate, a glass substrate, or a plastic substrate.

8. The sensor arrangement as claimed in claim 1, wherein
the first and/or the second temporally variable electrical signal is a temporally variable electrical voltage and the third temporally variable electrical signal is a temporally variable electric current; or
the first and/or the second temporally variable electrical signal is a temporally variable electric current and the third temporally variable electrical signal is a temporally variable electrical voltage.

9. The sensor arrangement as claimed in claim 1, wherein a time dependence of the first and/or of the second temporally variable electrical signal and/or a time dependence of the third temporally variable electrical signal is a mathematical sine function, rectangular function, sawtooth function, triangular function, or step function.

10. The sensor arrangement as claimed in claim 1, wherein in the control circuit the first electrical signal is a first temporally variable electrical signal and the second electrical signal is a constant reference potential; or
the second electrical signal is a second temporally variable electrical signal and the first electrical signal is a constant reference potential; or
the first electrical signal is a first temporally variable electrical signal, the second electrical signal is a second temporally variable electrical signal, the first and second temporally variable electrical signals being in antiphase with respect to one another.

11. The sensor arrangement as claimed in claim 10, wherein the electrical reference potential is the ground potential or a time average value of the first or of the second temporally variable electrical signal.

12. The sensor arrangement as claimed in claim 1, wherein the reference liquid is a different liquid than the analyte and is free of molecules to be detected.

13. The sensor arrangement as claimed in claim 1, wherein the reference liquid is the analyte, and in the sensor arrangement
the first operating state is a first time period, in which essentially no hybridization events have taken place; and
the second operating state is a second time period, temporally after the first time period, in which essentially all hybridization events have taken place.

14. The sensor arrangement as claimed in claim 1, further comprising an analog/digital converter circuit, which is integrated in the substrate, for converting an analog temporally variable electrical signal into a digital signal and providing the digital signal to the evaluation circuit.

15. The sensor arrangement as claimed in claim 1, further comprising an external supply unit, which provides the control circuit with electrical voltage signals and/or electric current signals.

16. The sensor arrangement as claimed in claim 15, further comprising a digital/analog converter circuit, which is integrated in the substrate, for converting a digital voltage signal and/or current signal of the external supply unit into an analog signal and providing the analog signal to the control circuit.

17. The sensor arrangement as claimed in claim 1, further comprising a selection circuit, which is integrated in the substrate, for sequentially selecting in each case one of the sensor electrodes.

18. The sensor arrangement as claimed in claim 1, wherein different capture molecules are immobilized on different sensor electrodes.

19. The sensor arrangement as claimed in claim 1, set up as a biosensor arrangement.

20. The sensor arrangement as claimed in claim 1, wherein the evaluation circuit determines, based on the reference value and the sensor value of the third temporally variable electrical signal and based on the first and/or second temporally variable electrical signal, the value of the impedance between the selected sensor electrode and an electrically conductive substance introduced into the sensor arrangement in the first operating state and in the second operating state.

21. The sensor arrangement as claimed in claim 1, wherein the evaluation circuit determines, based on the quotient of the values of the capacitance between the selected sensor electrode and an electrically conductive substance introduced into the sensor arrangement in the first operating state and in the second operating state, whether hybridization events have taken place at the selected sensor electrode and/or the quantity in which hybridization events have taken place at the selected sensor electrode.

22. The sensor arrangement as claimed in claim 1, wherein when the evaluation circuit is determining the values $\beta(i,j) C_{array}(i,j)$, the evaluation circuit uses at least one of the following approximations:

$$N * M \gg 1; \text{ and}$$

$$\sum_{x=1}^{N} \sum_{y=1}^{M} \beta(x,y) C_{array}(x,y) \gg \beta(n,m) C_{array}(n,m).$$

23. A method for operating a sensor arrangement, comprising:
providing a sensor arrangement, set up as an integrated circuit, having:
a substrate;
at least three sensor electrodes arranged on the substrate such that, in an operating state in which an electrically conductive substance is introduced into the sensor arrangement, the sensor electrodes are coupled to one another by means of the electrically conductive substance;
capture molecules immobilized on at least a portion of the sensor electrodes, wherein molecules to be detected can hybridize with the capture molecules;
a control circuit;
a detection device; and
an evaluation circuit;
the control circuit applying a first electrical signal to a selected sensor electrode and simultaneously applying a second electrical signal to at least two of the other sensor electrodes, the first electrical signal being a first temporally variable electrical signal and/or the second electrical signal being a second temporally variable electrical signal;
in a first operating state, in which a reference liquid is introduced into the sensor arrangement, the detector device detecting at the selected sensor electrode a reference value of a third temporally variable electrical signal resulting from the first temporally variable electrical signal and/or from the second temporally variable electrical signal;
in a second operating state, in which an analyte possibly having molecules to be detected is introduced into the sensor arrangement, the detector device detecting at the selected sensor electrode, a sensor value of a third temporally variable electrical signal resulting from the first temporally variable electrical signal and/or from the second temporally variable electrical signal; and
the evaluation circuit determining, on the basis of the reference value and the sensor value, whether a hybridization event has taken place at the selected sensor electrode,
wherein the evaluation circuit determines, based on the reference value and the sensor value of the third temporally variable electrical signal and based on the first and/or second temporally variable electrical signal, the value of the capacitance between the selected sensor electrode and an electrically conductive substance introduced into the sensor arrangement in the first operating state and in the second operating state, and
wherein the evaluation circuit determines, for at least a portion of the sensor electrodes, whether hybridization events have taken place at the selected sensor electrode and/or the quantity in which hybridization events have taken place at the selected sensor electrode, by determining the values $\beta(i,j) C_{array}(i,j)$ for the first and second operating states from the system of equations $$C_{meas}(n,m) = \beta(n,m) C_{array}(n,m) \times \left[ 1 - \frac{\beta(n,m) C_{array}(n,m)}{\sum_{x=1}^{N} \sum_{y=1}^{M} \beta(x,y) C_{array}(x,y)} \right]$$

where n,m are indices of a selected sensor electrode in the cell array;
where x,y are indices of the sensor electrodes in the cell array;
where N*M is the number of sensor electrodes in the cell array;
where $C_{array}(i,j)$ is the value of the capacitance between the sensor electrode having the indices i,j and the reference liquid in the first operating state;
where $\beta(i,j) C_{array}(i,j)$ is the value of the capacitance between the sensor electrode having the indices i,j and the analyte in the second operating state; and
where $C_{meas}(n,m)$ is the value of the capacitance determined between the selected sensor electrode having the indices n,m and an electrically conductive substance introduced into the sensor arrangement.

24. The method as claimed in claim 23, wherein the reference liquid is essentially the same substance as the analyte, except that the reference liquid is free of molecules to be detected.

25. A sensor arrangement, set up as an integrated circuit, comprising:
a substrate;
at least three sensor electrodes arranged on the substrate such that, in an operating state in which an electrically conductive substance is introduced into the sensor arrangement, the sensor electrodes are coupled to one another by means of the electrically conductive substance;
capture molecules immobilized on at least a portion of the sensor electrodes, wherein molecules to be detected can hybridize with the capture molecules;
a control means for applying a first electrical signal to a selected sensor electrode and simultaneously applying a second electrical signal to at least two of the other sensor electrodes, the first electrical signal being a first temporally variable electrical signal and/or the second electrical signal being a second temporally variable electrical signal;
a detection means, which is set up such that,
in a first operating state, in which a reference liquid is introduced into the sensor arrangement, a reference value of a third temporally variable electrical signal resulting from the first temporally variable electrical signal and/or from the second temporally variable electrical signal is detected at the selected sensor electrode; and
in a second operating state, in which an analyte possibly having molecules to be detected is introduced into the sensor arrangement, a sensor value of the third temporally variable electrical signal resulting from the first temporally variable electrical signal and/or from the second temporally variable electrical signal is detected at the selected sensor electrode; and an evaluation means, which, on the basis of the reference value and the sensor value, determines whether a hybridization event has taken place at the selected sensor electrodes, wherein the evaluation circuit determines, based on the reference value and the sensor value of the third temporally variable electrical signal and based on the first and/or second temporally variable electrical signal, the value of the capacitance between the selected sensor electrode and an electrically conductive substance introduced into the sensor arrangement in the first operating state and in the second operating state, and wherein the evaluation circuit determines, for at least a portion of the sensor electrodes, whether hybridization events have taken place at the selected sensor electrode and/or the quantity in which hybridization events have taken place at the selected sensor electrode, by determining the values $\beta(i,j)C_{array}(i,j)$ for the first and second operating states from the system of equations $$C_{meas}(n,m) = \beta(n,m)C_{array}(n,m) \times \left[1 - \frac{\beta(n,m)C_{array}(n,m)}{\sum_{x=1}^{N}\sum_{y=1}^{M} \beta(x,y)C_{array}(x,y)}\right]$$

where n,m are indices of a selected sensor electrode in the cell array;

where x,y are indices of the sensor electrodes in the cell array;

where N*M is the number of sensor electrodes in the cell array;

where $C_{array}(i,j)$ is the value of the capacitance between the sensor electrode having the indices i,j and the reference liquid in the first operating state;

where $\beta(i,j)C_{array}(i,j)$ is the value of the capacitance between the sensor electrode having the indices i,j and the analyte in the second operating state; and where $C_{meas}(n,m)$ is the value of the capacitance determined between the selected sensor electrode having the indices n,m and an electrically conductive substance introduced into the sensor arrangement.

26. A method for operating a sensor arrangement, which set up as an integrated circuit, and has a substrate, at least three sensor electrodes arranged on the substrate such that, in an operating state in which an electrically conductive substance is introduced into the sensor arrangement, the sensor electrodes are coupled to one another by means of the electrically conductive substance, capture molecules immobilized on at least a portion of the sensor electrodes, wherein molecules to be detected can hybridize with the capture molecules, a control circuit, a detection device, and an evaluation circuit, the method comprising:

the control circuit applying a first electrical signal to a selected sensor electrode and simultaneously applying a second electrical signal to at least two of the other sensor electrodes, the first electrical signal being a first temporally variable electrical signal and/or the second electrical signal being a second temporally variable electrical signal;

in a first operating state, in which a reference liquid is introduced into the sensor arrangement, the detector device detecting at the selected sensor electrode a reference value of a third temporally variable electrical signal resulting from the first temporally variable electrical signal and/or from the second temporally variable electrical signal;

in a second operating state, in which an analyte possibly having molecules to be detected is introduced into the sensor arrangement, the detector device detecting at the selected sensor electrode, a sensor value of a third temporally variable electrical signal resulting from the first temporally variable electrical signal and/or from the second temporally variable electrical signal; and the evaluation circuit determining, on the basis of the reference value and the sensor value, whether a hybridization event has taken place at the selected sensor electrode, wherein the evaluation circuit determines, based on the reference value and the sensor value of the third temporally variable electrical signal and based on the first and/or second temporally variable electrical signal, the value of the capacitance between the selected sensor electrode and an electrically conductive substance introduced into the sensor arrangement in the first operating state and in the second operating state, and wherein the evaluation circuit determines, for at least a portion of the sensor electrodes, whether hybridization events have taken place at the selected sensor electrode and/or the quantity in which hybridization events have taken place at the selected sensor electrode, by determining the values $\beta(i,j)C_{array}(i,j)$ for the first and second operating states from the system of equations $$C_{meas}(n,m) = \beta(n,m)C_{array}(n,m) \times \left[1 - \frac{\beta(n,m)C_{array}(n,m)}{\sum_{x=1}^{N}\sum_{y=1}^{M} \beta(x,y)C_{array}(x,y)}\right]$$

where n,m are indices of a selected sensor electrode in the cell array;

where x,y are indices of the sensor electrodes in the cell array;

where N*M is the number of sensor electrodes in the cell array;

where $C_{array}(i,j)$ is the value of the capacitance between the sensor electrode having the indices i,j and the reference liquid in the first operating state;

where $\beta(i,j)C_{array}(i,j)$ is the value of the capacitance between the sensor electrode having the indices i,j and the analyte in the second operating state; and where $C_{meas}(n,m)$ is the value of the capacitance determined between the selected sensor electrode having the indices n,m and an electrically conductive substance introduced into the sensor arrangement.

* * * * *